United States Patent
Joullié et al.

[11] Patent Number: 6,127,189
[45] Date of Patent: Oct. 3, 2000

[54] COMPOSITIONS AND METHODS FOR DETECTION OF AN AMINE COMPOUND IN A FINGERPRINT

[75] Inventors: Madeleine M. Joullié, Philadelphia; Diane Hauze, St. Davids; Olga Petrovskaia, Philadelphia, all of Pa.

[73] Assignee: The Trustees of the University of Pennsylvania, Philadelphia, Pa.

[21] Appl. No.: 08/966,252

[22] Filed: Nov. 7, 1997

Related U.S. Application Data

[60] Provisional application No. 60/030,240, Nov. 8, 1996.

[51] Int. Cl.⁷ ........................ G01N 33/00; C07C 49/633
[52] U.S. Cl. ........................ 436/111; 422/61; 422/68.1; 436/86; 436/89; 436/90; 436/112; 436/166; 436/172; 568/327; 568/330
[58] Field of Search ................ 422/61, 68.1, 82.05, 422/82.08, 82.09; 436/86, 89, 90, 111, 112, 164, 166, 172; 568/327, 330

[56] References Cited

U.S. PATENT DOCUMENTS

| | | | |
|---|---|---|---|
| 3,578,705 | 5/1971 | Wendler et al. | 568/327 X |
| 3,696,111 | 10/1972 | Juby et al. | 562/466 |
| 3,792,057 | 2/1974 | Jensen et al. | 260/309 |
| 4,431,647 | 2/1984 | McClure | 514/229.8 |
| 4,826,975 | 5/1989 | Picciola et al. | 544/391 |
| 5,708,018 | 1/1998 | Haadsma-Svensson et al. | 514/408 |

FOREIGN PATENT DOCUMENTS

| | | |
|---|---|---|
| 1025080 | 12/1958 | Germany . |
| 221930 | 6/1942 | Switzerland . |

OTHER PUBLICATIONS

M. Matsui et al. Agr.Biol. Chem. 1964, 28, 896–899.
M. Minessen–Guette et al. Bull. Soc. Chim. Fr. 1968, 2111–2117.
G. Simchen et al. Chem. Ber> 1969, 102, 3656–3665.
G. Eglite et al. Chem. Abstr. 1971, 75, abstract 29752f.
J.–Y. Lin et al. Agr. Biol. Chem. 1972, 36, 506–509.
R. T. Coutts et al. Can. J. Chem. 1974, 52, 381–389.
A. H. Jackson et al. J. Chem. Soc., Perkin Trans. 1 1974, 1911–1920.
H. Irie et al. J. Chem. Soc. Chem. Commun. 1975, 63.
J. Mukherjee et al. Chem. Abstr. 1975, 83, abstract 206060s.
T. Kametani et al. Chem. Pharm. Bull. 1975, 23, 2634–2642.
S. O. De Silva et al. Can. J. Chem. 1979, 57, 1598–1605.
R. M. Silverstein et al. "Spectrometric Identification of Organic Compounds" 4th ed. 1981, John Wiley & Sons: New York, pp. 305–329.
R. Singh et al. Indian J. Chem. 1989, 28B, 5–9.
R. R. Hark et al. Tetrahedron Lett. 1994, 35, 7719–7722.
A. P. Venkov et al. Synth. Commun. 1996, 26, 755–762.
Cava et al., 1958, J. Am. Chem. Soc. 80:2257–2263.
Chakravarti et al., 1934, J. Indian Chem. Soc. 11:101–104.
Del Castillo et al., 1991, In: Luminescence Techniques in Chemical and Biochemical Analysis, Practical Spectroscopy Series, vol. 12, Baeyens, ed. Marcel Dekker, Inc., New York, p. 90–103.
Grigg et al., 1990, Tetrahedron Lett. 31:7215–7218.
Herod, 1982, J. Forensic Sci. 27:513–518.
Ingold et al., 1923, J. Chem. Soc., 123:1476–1488.

(List continued on next page.)

*Primary Examiner*—Arlen Soderquist
*Attorney, Agent, or Firm*—Akin, Gump, Strauss, Hauer & Feld, L.L.P.

[57] ABSTRACT

The invention includes compositions comprising and methods of using 1,2-indanedione derivatives for detecting an amine compound such as an amino acid. Methods of detecting and recording the pattern of a fingerprint on a surface are also included, as are a kit for detecting an amine compound such as a constituent of a fingerprint. The invention further includes a device for developing a fingerprint and a method of making 1,2-indanedione derivatives.

62 Claims, 11 Drawing Sheets

(4 of 11 Drawing Sheet(s) Filed in Color)

1 - light source
2 - excitation filter
3 - excitation light
3' - reflected excitation light
4 - emission light (fluorescence)
5 - observation filter
6 - camera

OTHER PUBLICATIONS

Margot et al., 1993, In: Manual of Fingerprint Detection Techniques, 5th ed. University of Lausanne, Lausanne, Switzerland, p. 109.
Noyes et al., 1943, Organic Synthesis, John Wiley & Sons, Inc., p. 108–109.
Oden et al., 1954, Nature 173:449.
Perkin et al., 1912, J. Chem. Soc. 101:232–237.
Perkin et al., 1914, J. Chem. Soc. 105:2406–2408.
Ruhemann, 1910, Trans. Chem. Soc. 97:2025–2031.
Ruhemann, 1910, Trans. Chem. Soc. 97:1438–1449.
Tomchin et al., 1988, Zh. Org. Khim. 24:1827.
T. Lin et al. *SPIE* 1996, 2705, 190–198.
J. Kenner et al. *J. Chem. Soc.* 1921, 119, 1452–1461.
J. B. D. Mackenzie et al. *J. Chem. Soc.* 1949 497–499.
M. Cushman et al. *Tetrahedron* 1978, 34, 1435–1439.
V. Cavvini et al., *Eur. J. Med. Chem.–Chim, Ther.* 1979, 14, 343–346.
J. R. Merchant et al. *Indian J. Chem. Sect. B* 1984, 23B, 863–865.
K. Takeshita et al, Chem. Pharm. Bull. 1986, 34, 3919–3921.
C. B. Hudson et al. *Aust. J. Chem.* 1967, 20, 1511–1520.
F. Santavy et al. *Collect. Czech. Chem. Commun.* 1972, 37, 1825–1850.
S. K. Gupta et al. *J. Pharm. Sci.* 1976, 65, 134–135.
S. Huneck et al. *Phytochem.* 1976, 16, 1013–1016.
S. Y. Dike et al, *Indian J. Chem.* 1979, 17B, 336–338.
J. Almog et al, *J. Forens. Sci.* 1982, 27, 0912–0917.
R. L. Shriner et al. "The Systematic Identification of Organic Compounds" John Wiley & Sons, Inc., New York, 1980, pp. 242–243.
P. S. Hillery et al, *J. Am. Chem. Soc.* 1983, 105, 2760–2770.
C. J. Lennard et al. *J. Forensic Sci.* 1987, 32, 597–605.
J. Almog *J. Forensic Sci.* 1987, 32, 1565–1573.
C. J. Lennard et al, *J. Forensic Sci. Soc.* 1988, 28, 3–23.
E. R. Menzel et al. *J. Forensic Sci.* 1990, 35, 25–34.
J. Almog et al. *J. Forensic Sci.* 1992, 37, 688–694.
A. I. Mekkaoui et al. *J. Forensic Sci.* 1993, 38, 506–520.
P. J. Davies et al. *J. Forensic Sci* 1995, 40, 565–569.

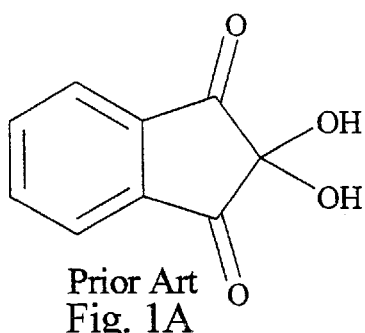
Prior Art
Fig. 1A
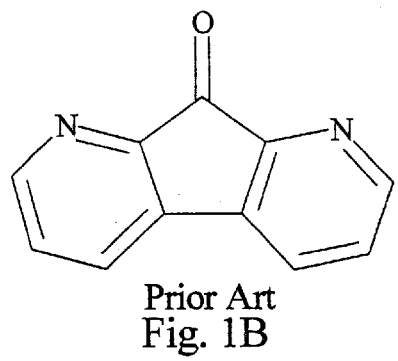
Prior Art
Fig. 1B
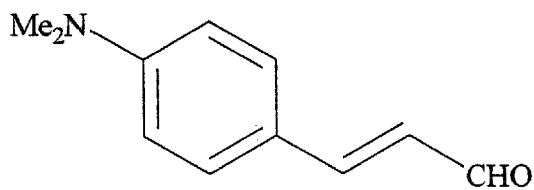
Prior Art
Fig. 1C
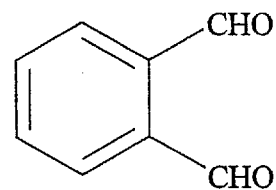
Prior Art
Fig. 1D
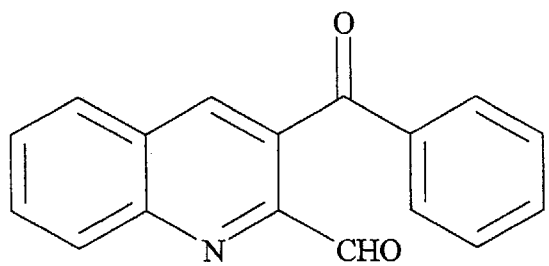
Prior Art
Fig. 1E
Fig. 1F
Prior Art
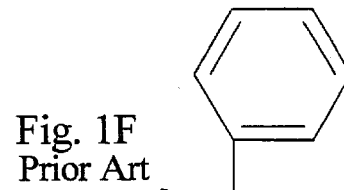
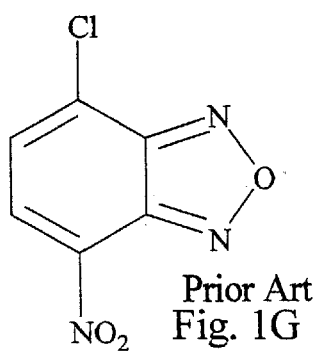
Prior Art
Fig. 1G
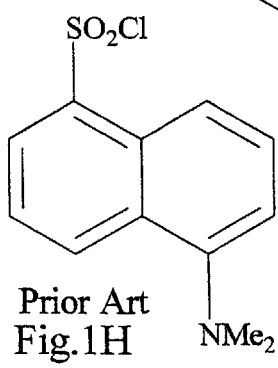
Prior Art
Fig. 1H 1 - light source
2 - excitation filter
3 - excitation light
3' - reflected excitation light
4 - emission light (fluorescence)
5 - observation filter
6 - camera

COMPOSITIONS AND METHODS FOR DETECTION OF AN AMINE COMPOUND IN A FINGERPRINT

CROSS REFERENCE TO RELATED APPLICATIONS

This application claims priority under 35 U.S.C. § 119(e) to U.S. Provisional Application No. 60/030,240, filed on Nov. 8, 1996.

GOVERNMENT INTEREST

Portions of this invention were supported in part by the U.S. Government (National Security Council Interagency Working Group on Terrorism Grant No. 96-P846900-000), and the U.S. Government may therefore have certain rights in the invention.

FIELD OF THE INVENTION

The field of the invention is detection of amine compounds.

BACKGROUND OF THE INVENTION

Chromogenic and fluorogenic reagents for detecting compounds having one or more amine functionalities have a wide range of uses. Examples of such uses include detection and quantitation of peptides, amines, amino sugars, or amino acids in solutions and on surfaces. Thus, these reagents are useful for performance of biochemical assays and detection of latent fingerprints, among other applications.

Owing to the importance of latent fingerprint development and identification, forensic scientists have synthesized and employed a variety of reagents for amino acid detection on solid surfaces. Fingerprint identification reagents ideally exhibit high selectivity for amine compounds compared with other components of fingerprints, high sensitivity so that minute amounts of amine compounds may be detected, and sharp line resolution so that fingerprint patterns may be identified. In addition, such reagents are ideally easy to apply to surfaces, require no secondary treatment, and can be synthesized at low cost.

Fingerprints are among the most important forms of physical evidence found at crime scenes and can permit the unquestionable identification of an individual. The ridge patterns on the fingers of humans are unique, substantially immutable, and easy to classify. However, fingerprints deposited on surfaces are seldom visible. Fingerprints comprise glandular secretions including amino acids, urea, fatty acids, glycerides, inorganic salts, and the like. These components are not ordinarily visible and do not display significant inherent absorbance or fluorescence in the visible region of the electromagnetic spectrum.

A typical fingerprint comprises about one microgram of organic and inorganic compounds, including from about 100 to about 250 nanograms of amine compounds such as amino acids. Of course, the amount of material deposited on a surface may vary considerably, depending on such factors as glandular activity and the pressure applied to the surface when the fingerprint is deposited. Highly sensitive methods are therefore necessary for detection of latent fingerprints. Chemical methods of fingerprint detection have been demonstrated to be more effective than optical, physical, or physico-chemical methods for detection of fingerprints deposited on porous surfaces such as wood or paper (Margot et al., 1993, In: *Manual of Fingerprint Detection Techniques*, 5th ed. University of Lausanne, Lausanne, Switzerland, p. 109).

The capacity of ninhydrin to react with amine compounds to yield a colored product makes it a useful reagent for detection of amino acids such as those present in latent fingerprints (Ruhemann, 1910, Trans. Chem. Soc. 97:1438–1449; Ruhemann, 1910, Trans. Chem. Soc. 97:2025–2031; Oden et al., 1954, Nature 173:449). Secondary treatment using zinc salts has been demonstrated to enhance the sensitivity of the ninhydrin method of detecting latent fingerprints (Herod, 1982, J. Forensic Sci. 27:513–518). Other compounds useful for visualizing the amino acids present in latent fingerprints have been described, including 1,8-diazafluoren-9-one (DFO; Grigg et al., 1990, Tetrahedron Lett. 31:7215–7218), silver nitrate, chloronitrobenzoxadiazole, o-phthalaldehyde, p-dimethylaminocinnamaldehyde, benzoylquinolinecarboxaldehyde, fluorescamine, dansyl chloride, and the like. The chemical structures of several of these compounds are depicted in FIG. 1. However, each of these reagents have particular disadvantages, as described (Margot et al., In: *Manual of Fingerprint Detection Techniques*, 5th ed. University of Lausanne, Lausanne, Switzerland, p. 109; Baeyens et al., 1991, In: *Luminescence Techniques in Chemical and Biochemical Analysis*, Practical Spectroscopy Series, vol. 12, Brame, ed. Marcel Dekker, Inc., New York, p. 654).

The most sensitive and widely used reagents for latent fingerprint detection are ninhydrin and DFO. Although ninhydrin is an excellent chromogenic compound, a print developed with ninhydrin fluoresces only after a secondary treatment with zinc chloride. Forensic investigators regard the secondary zinc chloride treatment as a significant drawback. Development of a fingerprint using DFO does not require secondary treatment and has superior fluorogenic properties relative to ninhydrin. However, the cost of DFO is prohibitive for most crime laboratories. Hence, there remains a significant need for a fingerprint detection reagent which has fluorogenic properties equivalent or superior to those of DFO, but is less expensive to synthesize. The present invention satisfies this need.

SUMMARY OF THE INVENTION

The invention relates to a method of detecting the presence of an amine compound comprising contacting the amine compound with a composition comprising a 1,2-indanedione derivative to form a product, assessing an optical property of the product, such as the absorbance or the fluorescence of the product, and comparing the optical property of the product with the same optical property of the composition, whereby a difference between the optical property of the product and the same optical property of the composition is an indication that the amine compound is present.

The 1,2-indanedione derivative preferably has the following chemical structure

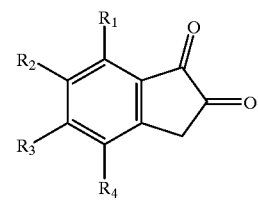

wherein $R_1$ and $R_4$ are independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_2$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_3$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent; and wherein the molecule is not 1,2-indanedione.

Preferably, the 1,2-indanedione derivative is selected from the group consisting of 1,2-indanedione, 6-methlythio-1,2-indanedione, 6-trimethylsilyl-1,2-indanedione, 6-nitro-1,2-indanedione, 5-methoxy-1,2-indanedione, 6-bromo-1,2-indanedione, 5-chloro-1,2-indanedione, 5,6,-dimethoxy-1,2-indanedione, 5-fluoro-1,2-indanedione, 6-(2-thienyl)-1,2-indanedione, 6-(3-thienyl)-1,2-indanedione, thieno[f]-1,2-indanedione, thieno[f]-2,3-indanedione, 5,6-methylenedioxy-1,2-indanedione, 5,6,7-trimethoxy-1,2-indanedione, a 2,2-substituted-1,3-dioxa-2-sila-cyclopenta[d]5,6-indanedione, 2,2-dimethyl-1,3-dioxa-2-sila-cyclopenta[d]5,6-indanedione, and indeno[2,3-e]benzofuran-1,2-dione. More preferably, the 1,2-indanedione derivative is selected from the group consisting of 5,6,-dimethoxy-1,2-indanedione and 5,6-methylenedioxy-1,2-indanedione.

In another aspect of the method of detecting the presence of an amine compound, the composition further comprises a group IIB metal cation. Preferably, the group IIB metal cation is a zinc cation.

In another aspect, the method of detecting the presence of an amine compound further comprises contacting the product with a group IIB metal cation prior to detecting fluorescence.

In yet another aspect of this method, the amine compound is a constituent of a human fingerprint on a surface, contacting the amine compound with the first composition comprises applying the first composition to the surface, and assessing an optical property of the product comprises illuminating the surface and observing the presence or absence of fluorescence.

In still another aspect of the method of detecting the presence of an amine compound, assessing an optical property of the product comprises illuminating the product using an electromagnetic radiation source which emits electromagnetic radiation having a wavelength less than about 530 nanometers. In this aspect, the method preferably further comprises detecting electromagnetic radiation emitted from the product having a wavelength greater than about 550 nanometers.

In another aspect, the method of detecting the presence of an amine compound further comprises applying heat and humidity to the product prior to assessing the optical property. Preferably, applying heat and humidity to the product comprises maintaining the product at about 40° C. and about 80% relative humidity for about one hour.

The invention also relates to a method of detecting a fingerprint on a surface comprising applying a first composition to the surface, the first composition comprising a 1,2-indanedione derivative, illuminating the surface, and assessing the presence or absence of fluorescence from the illuminated surface, whereby the fingerprint is detected by the presence of fluorescence emitted from the illuminated surface.

The invention also relates to a method of recording the pattern of a latent fingerprint on a surface comprising applying a first composition comprising a 1,2-indanedione derivative, illuminating the surface, whereby a fluorescence pattern is emitted from the surface, and recording the fluorescence pattern, whereby the pattern of the fingerprint is recorded.

The invention further relates to a composition of matter comprising a molecule having a chemical structure defined by formula I:

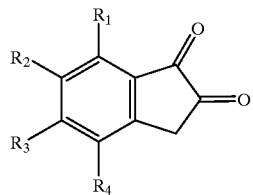

(I)

wherein $R_1$ and $R_4$ are independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_2$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_3$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent; and wherein the molecule is not 1,2-indanedione.

Preferably, the molecule is selected from the group consisting of 6-methlythio-1,2-indanedione, 6-trimethylsilyl-1,2-indanedione, 6-bromo-1,2-indanedione, 5-chloro-1,2-indanedione, 5-fluoro-1,2-indanedione, 6-(2-thienyl)-1,2-indanedione, 6-(3-thienyl)-1,2-indanedione, thieno [f]-1,2-indanedione, thieno[f]-2,3-indanedione, 5,6,7-trimethoxy-1,2-indanedione, a 2,2-substituted-1,3-dioxa-2-sila-cyclopenta[d]5,6-indanedione, 2,2-dimethyl-1,3-dioxa-2-sila-cyclopenta[d]5,6-indanedione, 4,5,6-trimethoxy-1,2-indanedione, and indeno[2,3-e]benzofuran-1,2-dione.

In one aspect, the composition further comprises a group IIB metal cation.

The invention also relates to method of making a molecule having the chemical structure of Formula I

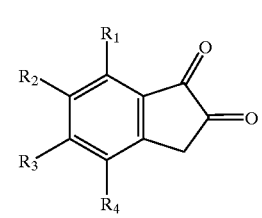

(I)

wherein each of $R_1$, $R_2$, $R_3$, and $R_4$ is independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent, the method comprising dissolving a 1-indanone derivative having the chemical structure of formula II in an acidic solvent,

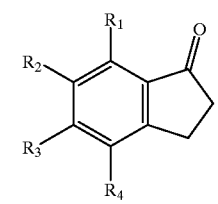

(II)

adding n-butyl nitrite to the solvent to form a precipitate, and contacting the precipitate with an acidic formaldehyde solution, whereby the molecule is formed.

The invention also relates to a kit for detecting the presence of an amine compound on a surface, the kit comprising an applicator and a composition of matter comprising a molecule having a chemical structure defined by formula I:

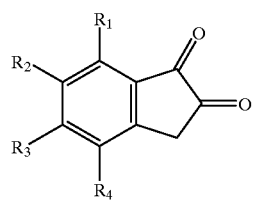

(I)

wherein $R_1$ and $R_4$ are independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_2$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_3$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent; and wherein the molecule is not 1,2-indanedione.

In one aspect of the kit of the invention, the composition further comprises a group IIB metal cation. In another aspect of the kit of the invention, the kit further comprises a second composition comprising a group IIB metal cation.

The invention further relates to a device for developing a fingerprint, the device comprising
a) a body having a surface for receiving the fingerprint,
b) a composition of matter associated with the body, the composition comprising a molecule having a chemical structure defined by formula I:

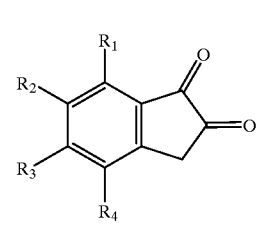

(I)

wherein $R_1$ and $R_4$ are independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_2$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_3$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent; and wherein the molecule is not 1,2-indanedione; and c) an applicator associated with the surface for applying the composition to the surface, whereby the fingerprint pattern is developed.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 1 comprising FIGS. 1A, 1B, 1C, 1D, 1E, 1F, 1G, and 1H, depicts the chemical structures of several reagents known in the prior art to be useful for detection of amino acids.

FIG. 1A depicts ninhydrin, FIG. 1B depicts 1,8-diazafluorenone (DFO); FIG. 1C depicts p-dimethylaminocinnamaldehyde; FIG. 1D depicts o-phthalaldehyde; FIG. 1E depicts 3-benzoyl-2-quinolinecarboxaldehyde; FIG. 1F depicts flurescamine; FIG. 1G depicts 4-chloro-7-nitrobenzo-2-oxa-1,3,-diazole (NBD-Cl); FIG. 1H depicts 5-demethylaminonaphthalene-1-sulfonylchloride (dansyl chloride).

Figure 2:
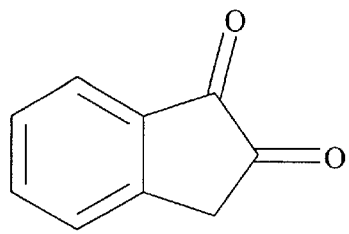
FIG. 2 depicts the chemical structure of 1,2-indanedione.

Compositions and conditions are described in the Example herein.

DETAILED DESCRIPTION OF THE INVENTION

The present invention includes compositions and methods for detecting amine compounds. An amine compound is a compound having an amino group.

The composition of the invention includes 1,2-indanedione derivatives having a chemical structure defined by formula I:

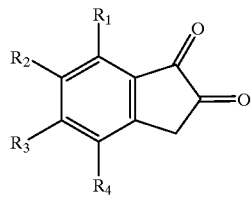

(I)

wherein each of $R_1$, $R_2$, $R_3$, and R4 is independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent.

The chemical structure and methods of synthesizing 1,2-indanedione and certain derivatives thereof, including 4,7-dimethyl-1,2-indanedione, 4-methyl-7-chloro-1,2-indanedione, 6-nitro-1,2-indanedione, 5-methoxy-1,2-indanedione, 5,6-dimethoxy-1,2-indanedione, 5,6-methylenedioxy-1,2-indanedione, and 3,3-diphenyl-1,2-indanedione, have been described (Cava et al., 1958, J. Am. Chem. Soc. 80:2257–2263; Perkin et al., 1912, J. Chem. Soc. 101:232–237; Ingold et al., 1923, J. Chem. Soc., 123:1476–1488; Chakravarti et al., 1934, J. Indian Chem. Soc. 11:101–104; Perkin et al., 1914, J. Chem. Soc. 105:2406–2408). However, other 1,2-indanediones described herein have not been described previously. Furthermore, compositions comprising a group IIB metal cation, and a 1,2-indanedione or a derivative thereof have not been previously described. Group IIB metals are metals which are listed in group IIB of the periodic table of the elements, and include zinc, cadmium, and mercury.

The invention includes a composition comprising a molecule having a chemical structure defined by formula I:

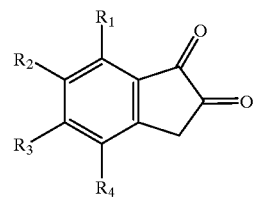

(I)

wherein $R_1$ and $R_4$ are independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_2$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_3$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent; and wherein the molecule is not 1,2-indanedione.

Figure 10:
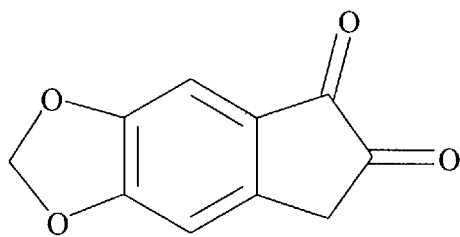
FIG. 10 depicts the chemical structure of 5,6-methylenedioxy-1,2-indanedione.

It is understood that any two or more of $R_{1-4}$ may be the same substituent, wherein the substituent is capable of forming two or more chemical bonds to the chemical structure of formula I. Thus, by way of example, when the molecule is 5,6-methylenedioxy-1,2-indanedione, $R_2$ and $R_3$ are both the same methylenedioxy substituent, as depicted in FIG. 10. It is further understood that the terms "aryl substituent" and "heteroaryl substituent" refer both to substituents which are monocyclic and substituents which are polycyclic.

In particular, a composition is contemplated which comprises a molecule selected from the group consisting of 6-methlythio-1,2-indanedione, 6-trimethylsilyl-1,2-indanedione, 6-bromo-1,2-indanedione, 5-chloro-1,2-indanedione, 5-fluoro-1,2-indanedione, 6-(2-thienyl)-1,2-indanedione, 6-(3-thienyl)-1,2-indanedione, thieno[f]-1,2-indanedione, thieno[f]-2,3-indanedione, 5,6,7-trimethoxy-1,2-indanedione, a 2,2-substituted-1,3-dioxa-2-sila-cyclopenta[d]5,6-indanedione, 2,2-dimethyl-1,3-dioxa-2-sila-cyclopenta[d]5,6-indanedione, 4,5,6-trimethoxy-1,2-indanedione, and indeno[2,3-e]benzofuran-1,2-dione. The chemical structures of each of these compounds are depicted in FIGS. 3 through 19.

Figure 15:
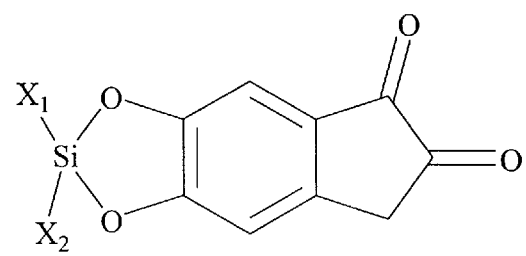
FIG. 15 depicts the chemical structure of a 2,2-substituted-1,3-dioxa-2-sila-cyclopenta[d]5,6-indanedione. When $X_1$ and $X_2$ are each a methyl group, the chemical structure is that of 2,2-dimethyl-1,3-dioxa-2-sila-cyclopenta[d]5,6-indanedione.
Figure 16:
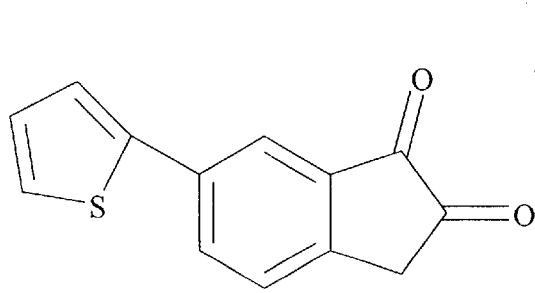
FIG. 16 depicts the chemical structure of 6-(2-thienyl)-1,2-indanedione.
Figure 17:
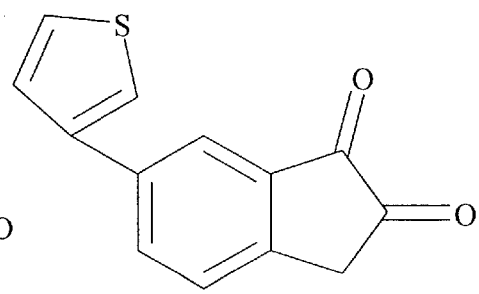
FIG. 17 depicts the chemical structure of 6-(3-thienyl)-1,2-indanedione.
Figure 18:
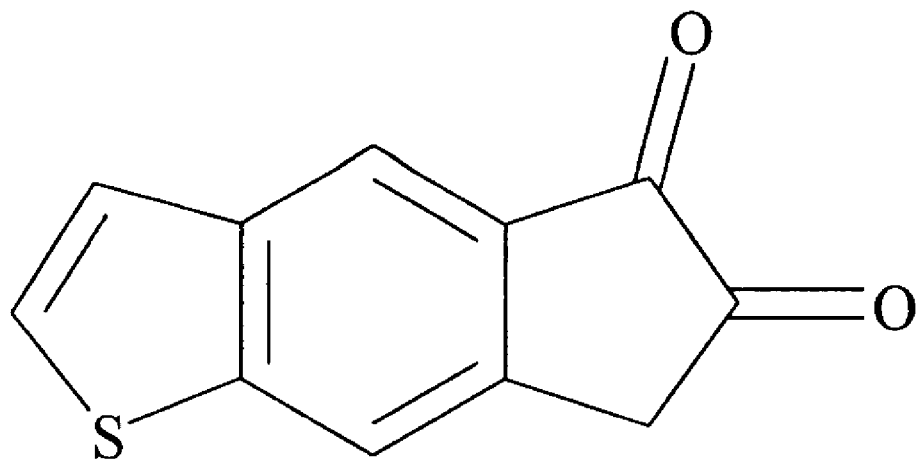
FIG. 18 depicts the chemical structure of thieno[f]-1,2-indanedione.
Figure 19:
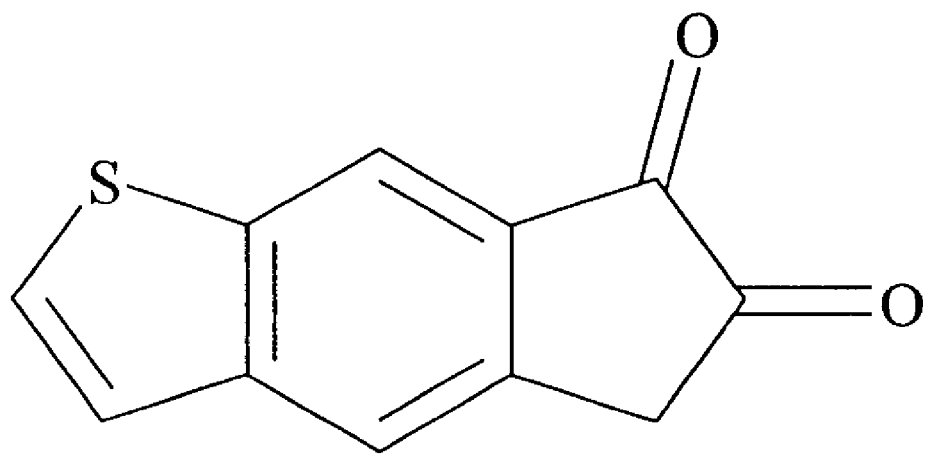
FIG. 19 depicts the chemical structure of thieno[f]-2,3-indanedione.

2,2-substituted-1,3-dioxa-2-sila-cyclopenta[d]5,6-indanediones have the chemical structure depicted in FIG. 15, wherein $X_1$ and $X_2$ are the same constituent or different constituents. $X_1$ and $X_2$ may each be any substituent(s) capable of forming a single bond with the Si atom of the a 2,2-substituted-1,3-dioxa-2-sila-cyclopenta[d]5,6-indanedione including, but not limited to, a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent. Thus, by way of example, $X_1$ and $X_2$ may be a methyl group and an ethyl group, respectively, may both be methyl groups, or may be different atoms in an aromatic heterocyclic ring. $X_1$ and $X_2$ may also together be a single substituent bonded to the Si atom of the a 2,2-substituted-1,3-dioxa-2-sila-cyclopenta[d]5,6-indanedione by a double bond. Thus, by way of example, $X_1$ and $X_2$ may also together be an oxygen atom bonded to the Si atom of the a 2,2-substituted-1,3-dioxa-2-sila-cyclopenta[d]5,6-indanedione by a double bond.

The composition may be a solution of a 1,2-indanedione derivative. By way of example, the composition may comprise a 0.1–0.2% (w/v) solution of a 1,2-indanedione derivative in methanol. Two compositions which are contemplated are designated Composition I and Composition II and have the following components.

Figure 8:
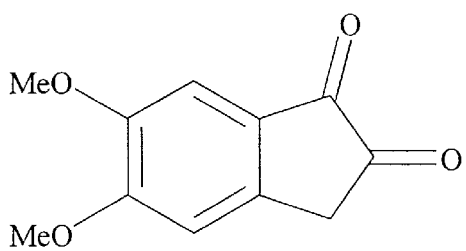
FIG. 8 depicts the chemical structure of 5,6-dimethoxy-1,2-indanedione.

Composition I
  0.05 grams of a 1,2-indanedione derivative
  50 milliliters methanol
  0.5 milliliters glacial acetic acid Composition II
  0.05 grams of a 1,2-indanedione derivative
  0.25 grams Zinc chloride
  50 milliliters methanol
  0.5 milliliters glacial acetic acid Two compositions which are particularly contemplated are a composition comprising 5,6-dimethoxy-1,2-indanedione, the chemical structure of which is depicted in FIG. 8, and a composition comprising 5,6-methylenedioxy-1,2-indanedione, the chemical structure of which is depicted in FIG. 10.

specific protocols for making specific examples of compositions described herein are disclosed in the Example. Methods of making each of the compositions of the invention are well within the knowledge of the skilled artisan given the disclosure herein.

The composition of the invention is useful in the methods of the invention, which are now described.

The invention includes a method of detecting an amine compound. The method comprises contacting the amine compound with the composition of the invention to form a product and thereafter assessing an optical property of the product. The optical property of the product is then compared with the same optical property of the composition, whereby the amine compound is detected by detecting a difference between the optical property of the product and the optical property of the composition.

The method of contacting the amine compound with the composition of the invention is not critical; any method which permits a molecule of the amine compound to interact with the molecule of the composition can be used. By way of example, if the amine compound is in a solution, then the composition may be mixed with the solution comprising the amine compound to permit contact between the amine compound and the molecule of the composition. If the solution and the composition of the invention are miscible, then the mixing the solution and the composition may be achieved, for example, by gently swirling a test tube containing the solution and the composition. If the solution and the composition of the invention are not miscible, then it may be advantageous to subject the solution and the composition to more vigorous mixing. By way of example, a test tube containing a solution and a composition of the invention which is not miscible with the solution can be mixed by pressing the tube against the actuator of a benchtop vortex mixer.

Further by way of example, if the amine compound is on a surface of an object, then the composition of the invention may be contacted with the amine compound by applying the composition to the surface. The method of applying the composition to the surface is not critical; any method of applying the composition to the surface can be used. Preferably, the method of applying the composition to the surface results in complete coverage of the surface by the composition using a minimal amount of the composition. By way of example, the composition may be applied to a surface by swiping a capillary tube coated with the composition across the surface, by directing a stream of atomized droplets comprising the composition at the surface, by directing a stream of atomized droplets comprising the composition above the surface and permitting them to fall upon the surface by the action of gravity, by brushing the surface using a brush coated with the composition, by pouring the composition in the form of a bulk liquid onto the surface, by immersing the surface in the composition, by exposing the surface to a gaseous or vaporized form of the composition, and the like.

The optical property may be any optical property that can be measured, and is preferably selected from the group consisting of absorbance and fluorescence. It is well known that the absorbance of a composition in the visual range of the electromagnetic spectrum may be assessed visually by a human, and is perceived as the color of the composition. A difference between an optical property of the product and an optical property of the composition of the invention may be characterized by contacting the composition with a known amine compound such as glycine to form a product, and then comparing the optical properties of the product with those of the composition.

By way of example, when the composition and the product formed by contacting the composition and the amine compound have absorbance spectra which differ in the visible region of the spectrum, the product can be differentiated from the composition because the two appear to the human eye to have different colors. For example, when the composition consists of about 1 millimolar 5-fluoro-1,2-indanedione in a 99:1 (volume:volume) mixture of methanol:glacial acetic acid, the composition is light yellow, but a product formed by contacting the composition with an amine compound has a light purple color. Thus, an amine compound can be detected by detecting the development of light purple color after contacting the amine compound with a composition which consists of about 1 millimolar 5-fluoro-1,2-indanedione in a 99:1 (volume:volume) mixture of methanol:glacial acetic acid.

Further by way of example, when the composition and the product formed by contacting the composition and the amine compound exhibit different fluorescent intensities when illuminated with radiation having a given wavelength, the product can be differentiated from the composition by assessing fluorescent intensity upon illumination by radiation having the given wavelength. For example, upon illumination with light having a wavelength of about 560 nanometers, a composition consisting of about 1 millimolar 5,6-dimethoxy-1,2-indanedione in a 99:1 (volume:volume) mixture of methanol:glacial acetic acid exhibits no appreciable fluorescence at about 575 nanometers. However, the product formed by contacting this composition with an amine compound exhibits significant fluorescence at about 575 nanometers upon illumination with light having a wavelength of about 560 nanometers. Thus, an amine compound can be detected by contacting the amine compound with the composition consisting of about 1 millimolar 5,6-dimethoxy-1,2-indanedione in a 99:1 (volume:volume) mixture of methanol:glacial acetic acid, and thereafter detecting fluorescence at about 575 nanometers upon illumination with light having a wavelength of about 560 nanometers.

The invention includes any method of assessing an optical property of the product and the same optical property of the composition. By way of example, it may be determined that a composition of the invention is normally colorless when the composition is applied to a surface such as filter paper, and that a product formed by contacting the composition and an amine compound has a color. One important use of the method of detecting an amine compound is a method of detecting a fingerprint. The method of detecting a fingerprint may be performed by applying the composition to a piece of filter paper, whereby the composition forms a product when contacted with an amine compound normally found in a fingerprint on the paper. Color development on the paper is then assessed, whereby the colored region(s) of the paper indicate the presence of a fingerprint.

When assessing an optical property of the product comprises assessing color development for example, the development of color may be assessed visually with the naked eye alternatively, the development of color may be assessed visually using a light filter which transmits only light having a wavelength in a particular range of values or by using a spectrophotometer to measure reflected light. Any other method known in the art for detection of color may be used. The color observed depends upon the molecule of the composition of the invention, as described in Table 2.

When assessing an optical property of the product comprises assessing absorbance of the product for example, absorbance may be assessed visually where the absorbance occurs within the visual region of the electromagnetic spectrum, using a spectrophotometer to measure reflected or transmitted light, or by any other method known in the art.

When assessing an optical property of the product comprises assessing fluorescence of the product for example, fluorescence may be assessed visually where the light emitted by the product is within the visual region of the electromagnetic spectrum, using a fluorescence spectrophotometer, by illuminating the product with light of one wavelength and assessing emission at a second wavelength, or by any other method known in the art.

It has been discovered that the addition of a group IIB metal cation enhances the fluorescent intensity of the product formed by contacting the composition of the invention and an amine compound. The presence of the cation also prolongs the duration of the fluorescence of the product. Thus, the composition of the invention may further comprise a group IIB metal cation such as $Zn^{++}$, $Cd^{++}$, or $Hg^{++}$. The cation is preferably $Zn^{++}$. The group IIB metal cation may be provided in the form of a group IIB metal salt, such as zinc chloride, zinc nitrate, or zinc nitrate. Any anion which permits dissolution of the metal cation in the composition of the invention may be used. The metal cation may be contacted with the product after product formation or with an amine compound prior to forming a product by contacting the amine compound and the composition of the invention.

It has furthermore been discovered that the sensitivity of the method of detecting an amine compound described herein can be improved by subjecting the product formed by contacting the amine compound and the composition of the invention to heat and humidity greater than normal ambient heat and humidity.

By way of example, the sensitivity of the method may be improved by maintaining the product at 40° C. and 80% relative humidity for about an hour prior to assessing the optical property of the product.

By way of example, the sensitivity of the method of detecting an amine compound described herein can be improved by contacting a product formed by contacting the composition of the invention and the amine compound with steam prior to assessing an optical property of the product. A hand-held steam iron of the type intended for use in pressing articles of clothing can be held from about twenty to about thirty seconds in close proximity, meaning from about one centimeter to about two centimeters, to a surface which bears an amine compound such as a constituent of a fingerprint and to which the composition of the invention has been applied. Thereafter, an optical property such as fluorescence of the product formed by contacting the amine compound and the composition may be assessed. The intensity of fluorescence of the product is greater following this steam treatment than the intensity prior to steam treatment. Increased fluorescent intensity following steam treatment means that the minimum quantity of an amine compound that can be detected using the method of the invention including a steam treatment step is smaller than the minimum quantity that can be detected using the method not including a steam treatment step. Thus, steam treatment increases the sensitivity of the method. Any other known method of applying heat and humidity to a surface may be used in the method of the invention to improve the sensitivity of the method.

Figure 22:
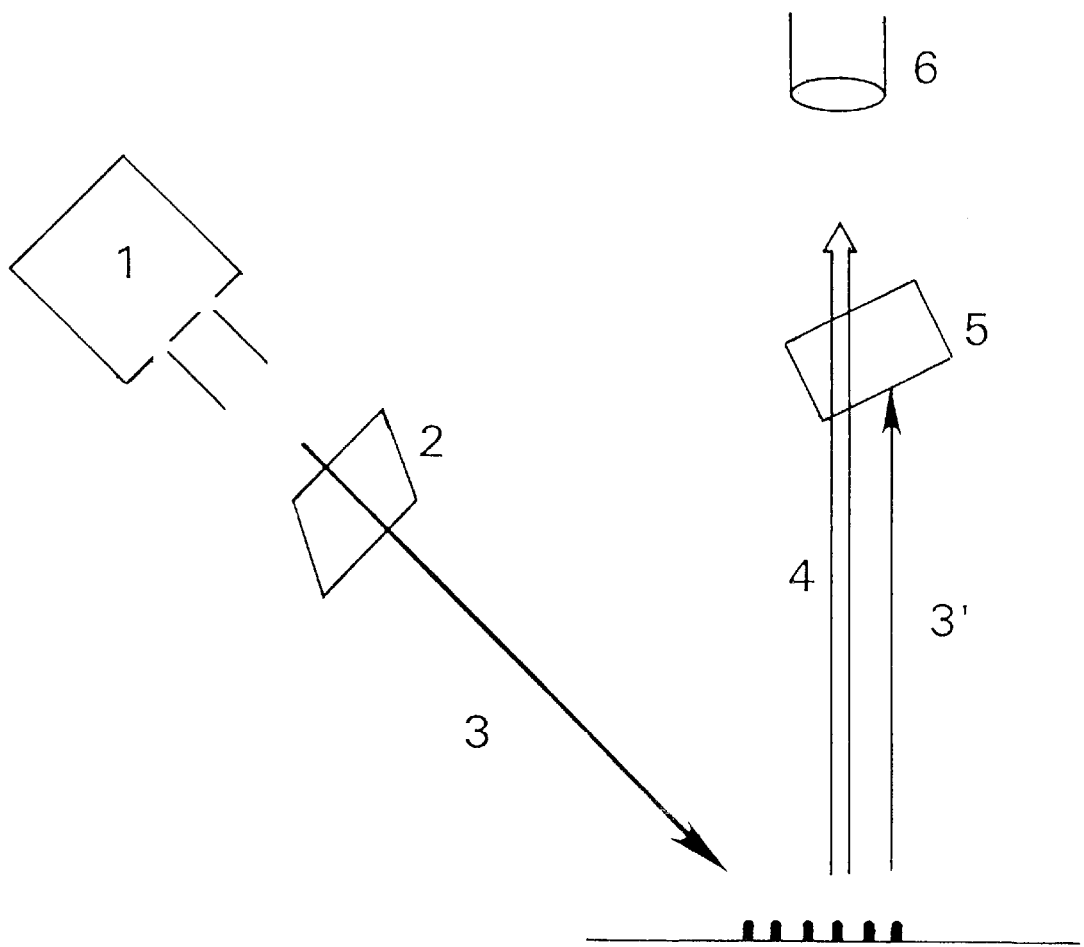
FIG. 22 depicts a method of visualizing a latent fingerprint developed with a 1,2-indanedione derivative, the method involving illumination of the fingerprint with an excitation light source and detection of light fluorescently emitted by the 1,2-indanedione-developed fingerprint using a camera.

A method for detecting a fingerprint on a surface is also included in the invention, and is illustrated in FIG. 22. The method comprises applying the composition of the invention to the surface, illuminating the surface, and detecting the presence or absence of fluorescence emitted from the illuminated surface, whereby the fingerprint is detected by detection of fluorescence emitted from the illuminated surface.

The method of applying the composition to the surface is not critical. Any method of applying the composition to the surface can be used, so long as the method permits the molecule of the composition to form a product with an amine compound in the fingerprint. Preferably, the method of applying the composition to the surface results in complete coverage of the surface by the composition using a minimal amount of the composition. By way of example, the composition may be applied to the surface by swiping a capillary tube coated with the composition across the surface, by directing a stream of atomized droplets comprising the composition at the surface, by directing a stream of atomized droplets comprising the composition above the surface and permitting them to fall upon the surface by the action of gravity, by brushing the surface using a brush coated with the composition, by pouring the composition in the form of a bulk liquid onto the surface, by immersing the surface in the composition, and the like.

The method of illuminating the surface is likewise not critical, except that the radiation with which the surface is illuminated must include radiation having a wavelength corresponding to an excitation wavelength of the product. Wavelengths which are excitation wavelengths for several molecules of the composition of the invention are listed, for example, in Table 2. For molecules of the composition of the invention which are not listed in Table 2, an excitation wavelength which is useful for inducing fluorescent emission of any particular molecule of the composition of the invention may be determined using well known methods. The method of illuminating the surface may, for example, comprise permitting ambient light to fall upon the surface, directing a light source at the surface, directing a light source equipped with an optical filter which transmits only light having a wavelength in a particular range, by directing a monochromatic light source such as a laser at the surface, and the like.

The method of detecting fluorescence from the illuminated surface is not critical; any method which is capable of detecting fluorescence emitted from a surface may be used. By way of example, the surface may be visually observed, an optical filter which transmits only light having a wavelength in a particular range may be placed between the surface and a viewer, a photodetector may be used to detect emitted light, and the like.

One preferred method of illuminating the surface and detecting fluorescence emitted from the surface comprises illuminating the surface with green light and observing red light emitted from the surface. For example, a white light source may be fitted with a first optical filter which does not substantially transmit light having a wavelength greater than about 530 nanometers, and light may be transmitted from the light source through the first optical filter and onto the surface. Light emitted from the surface may be observed using a detector fitted with a second optical filter which does not substantially transmit light having a wavelength less than about 550 nanometers. Thus, light which is merely reflected from the surface is only minimally detected, if at all. The detector may be a human eye, a camera, a photomultiplier tube, or the like.

The invention further includes a method of recording the pattern of a latent fingerprint on a surface comprising applying the composition of the invention to the surface. The molecule of the composition and an amine compound in the latent fingerprint form a product which fluoresces upon illumination with radiation having an excitation wavelength. Following application of the composition to the surface, the surface is illuminated with radiation having the excitation wavelength, and the product fluoresces, whereby a fluorescence pattern is emitted from the surface. A recorder such as a camera or a piece of radiation-sensitive film is used to record the fluorescence pattern.

The invention also includes a kit for detecting a latent fingerprint comprising the composition of the invention and an applicator for applying the composition to a surface. The applicator may be any device which is useful for applying the composition to a surface. For example, the applicator may be a capillary tube which can be coated with the composition, a brush which can be coated with the composition, an atomizer which can be used to atomize the composition, a sponge or other absorbent material which can absorb the composition, a film, plate, or other object to which the composition can be adsorbed, a container having an outlet for directing flow of a gaseous or vaporized form of the composition, and the like. The kit may also comprise a second composition which comprises a group IIB metal cation, such as a composition which comprises a group IIB metal salt such as zinc chloride, zinc acetate, or zinc nitrate. The kit of the invention may also include one or more optical filters, a light source, or a recorder. The recorder may be a camera such as a disposable camera, and may comprise an optical filter which transmits only radiation having a wavelength greater than about 550 nanometers, self-developing film such as Polaroid™ instant film, or film which is sensitive only to radiation having a wavelength greater than about 550 nanometers.

The kit of the invention can be used as follows. The applicator is contacted with the composition if the applicator is not supplied in contact with the composition. The applicator comprising the composition is contacted with the surface, whereby the composition is imparted from the applicator to the surface, and the molecule of the composition and an amine compound in the latent fingerprint form a product which fluoresces upon illumination with radiation having an excitation wavelength. The surface is illuminated with radiation having the excitation wavelength, and the latent fingerprint is detected by detecting fluorescence of the product. When the kit further comprises a second composition comprising a group IIB metal cation, the second composition may be applied to the surface before, simultaneously with, or after application of the first composition to the surface. Alternately, the second composition may be mixed with the composition of the invention prior to application of the mixture to the surface.

The invention also includes a device for developing a fingerprint pattern. The device of the invention comprises a body having a surface for receiving the fingerprint, an applicator associated with the surface, and the composition of the invention associated with the body. The composition may be in contact with the applicator or it may be in a reservoir, whereby the applicator is movable from a position in which it is in contact with the composition to a position in which it is in contact with the surface. The applicator is capable of depositing the composition onto the surface, whereby the fingerprint pattern is developed. Thus, in one embodiment of the device of the invention, the applicator is an atomizer mounted in relation to the surface such that when the composition is atomized using the atomizer, a stream of atomized droplets comprising the composition is directed at the surface or above the surface whereupon it may fall under the influence of gravity. In another embodiment, the applicator is a cylinder slidably mounted with respect to the surface, such that the composition may be applied to the surface of the cylinder and the cylinder may be slid or rolled across the surface in a direction perpendicular to the long axis of the cylinder, whereby the composition is transferred from the cylinder to the surface. In yet another embodiment of the device of the invention, the applicator is a brush which is movably mounted to the body, such that the brush may be moved between a reservoir containing the composition and the surface. In still another embodiment of the device of the invention, the device further comprises a viewer or a recorder, whereby the surface may be viewed or recorded following application of the composition to the surface. The viewer or recorder may be an optical lens, a camera, a digital camera, or the like, whereby the fluorescence pattern of a fingerprint on the surface may be viewed, recorded, or both, following application of the composition to the surface. The surface may be separable from the body, and may be, for example a sheet of filter paper mounted on the body.

The invention also comprises a method of making a 1,2-indanedione derivative having the chemical structure depicted in Formula I.

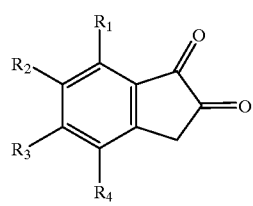

(I)

wherein $R_1$ and $R_4$ are independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_2$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an alkoxy substituent, a methoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent;

wherein $R_3$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, an unsubstituted heteroaryl substituent, and a substituted substituent; and wherein the molecule is not 1,2-indanedione. The method comprises performing α-oximation of a 1-indanone derivative having the chemical structure depicted in Formula II to yield a 1,2-indanedione-2-oxime derivative having the chemical structure depicted in Formula III and subsequently hydrolyzing the 1,2-indanedione-2-oxime derivative to yield the 1,2-indanedione derivative, wherein $R_{1-4}$ have the same meanings as in Formula I.

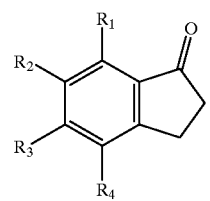

(II)

-continued

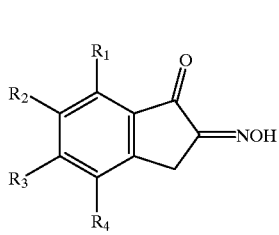

(III)

Figure 20:
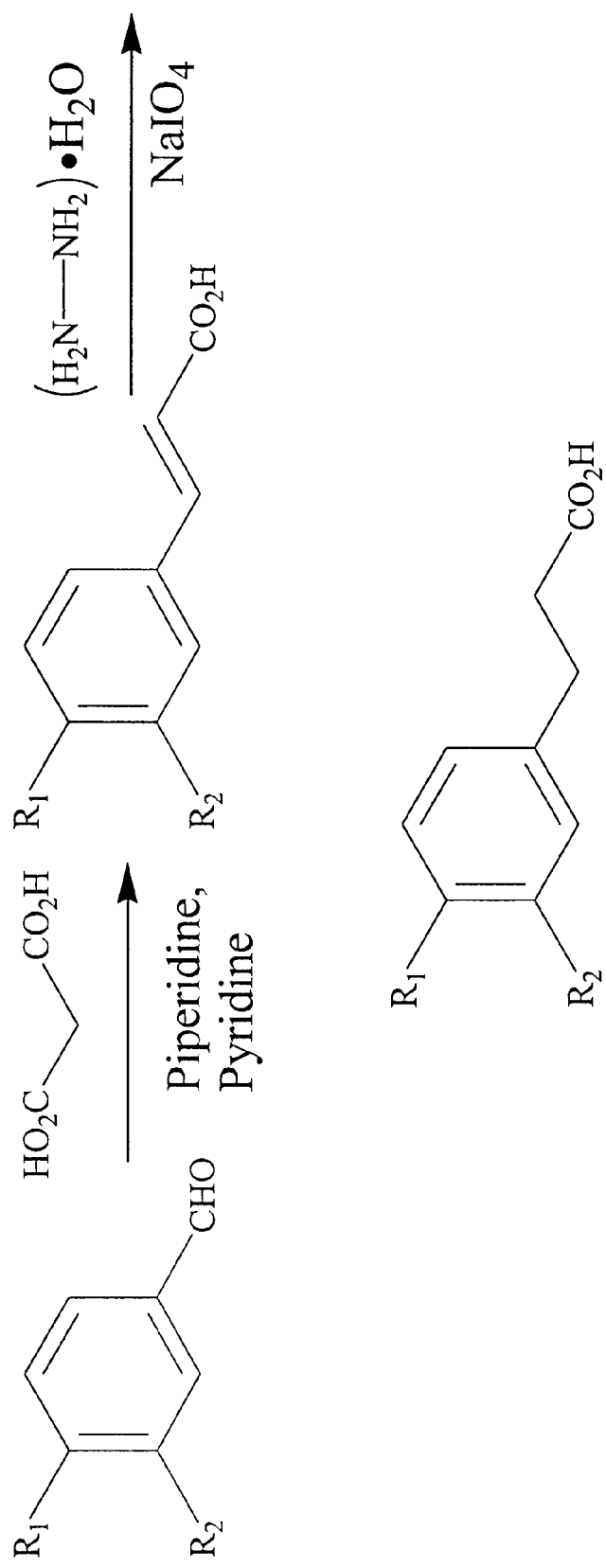
FIG. 20 illustrates a method of synthesizing a 1-indanone derivative.

The reagents and reactions conditions useful for performing α-oximation of a 1-indanone derivative and for hydrolyzing a 1,2-indanedione-2-oxime derivative have been described (Cava et al., 1958, J. Am. Chem. Soc. 80:2257–2263) and are summarized in FIG. 21. Methods of synthesizing 1-indanone derivatives are known in the art, and include Friedel-Crafts cyclization of phenyl propionic acid derivatives, as illustrated in FIG. 20 (Tomchin et al., 1988, Zh. Org. Khim. 24:1827). 1-Indanone derivatives and phenyl propionic acid derivatives are commercially available and can furthermore be synthesized using known methods.

The invention is now described with reference to the following Example. This Example is provided for the purpose of illustration only and the invention should in no way be construed as being limited to this Example but rather should be construed to encompass any and all variations which become evident as a result of the teaching provided herein.

EXAMPLE 1,2-Indanediones: New Reagents for Visualizing Amine Compounds Such as Those in Latent Fingerprints Compositions comprising 1,2-indanedione derivatives were examined and determined to be reagents which could be used to detect amine compounds and which were superior to known amine compound detection reagents.

The 1,2-indanediones which were investigated in the experiments presented in this Example are listed in Table 1.

TABLE 1

1,2-indanedione derivatives investigated in Example 1

Figure 3:
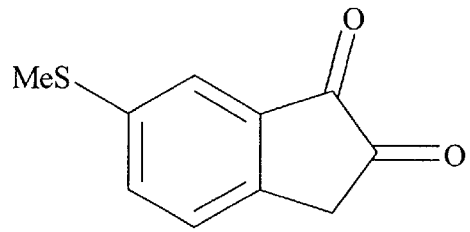
FIG. 3 depicts the chemical structure of 6-methylthio-1,2-indanedione.
Figure 4:
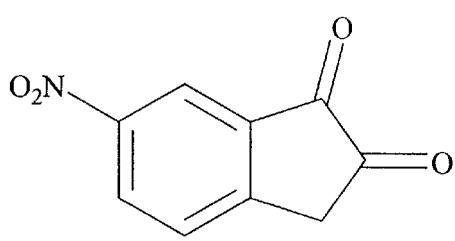
FIG. 4 depicts the chemical structure of 6-nitro-1,2-indanedione.
Figure 5:
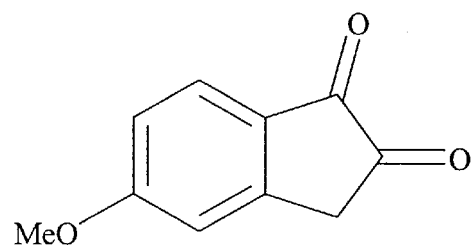
FIG. 5 depicts the chemical structure of 5-methoxy-1,2-indanedione.
Figure 6:
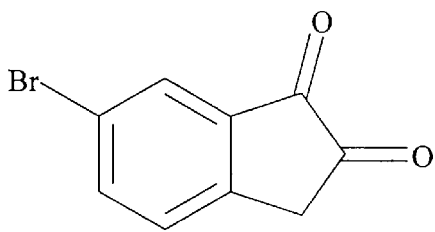
FIG. 6 depicts the chemical structure of 6-bromo-1,2-indanedione.
Figure 7:
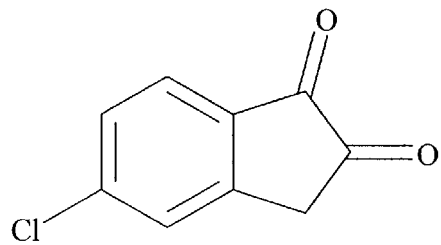
FIG. 7 depicts the chemical structure of 5-chloro-1,2-indanedione.
Figure 9:
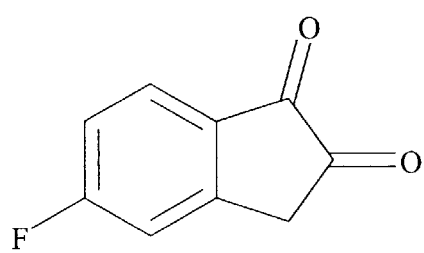
FIG. 9 depicts the chemical structure of 5-fluoro-1,2-indanedione.
Figure 11:
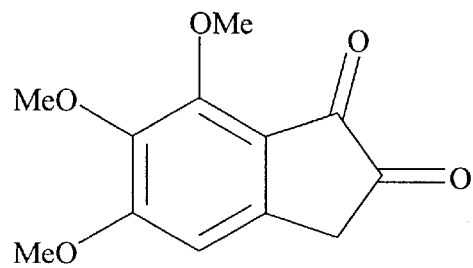
FIG. 11 depicts the chemical structure of 5,6,7-trimethoxy-1,2-indanedione.
Figure 12:
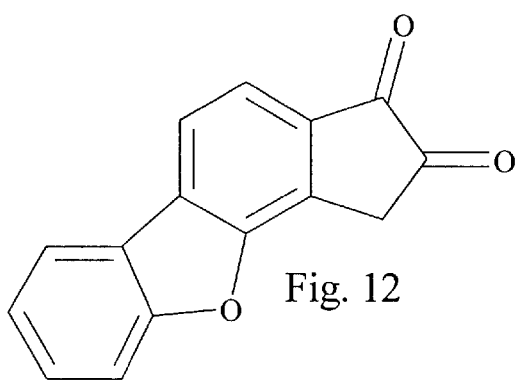
FIG. 12 depicts the chemical structure of indeno[2,3-e]benzofuran-1,2-dione.
Figure 13:
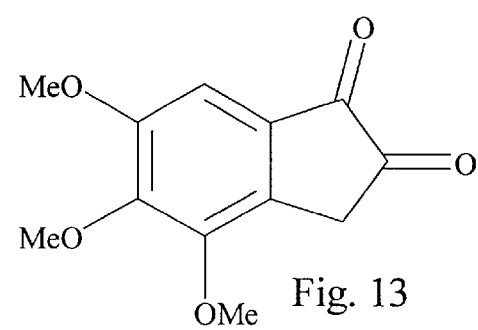
FIG. 13 depicts the chemical structure of 4,5,6-trimethoxy-1,2-indanedione.
Figure 14:
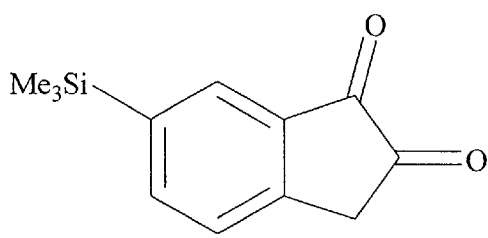
FIG. 14 depicts the chemical structure of 6-trimethylsilyl-1,2-indanedione.

1,2-indanedione, which has the chemical structure depicted in Figure 2
6-methylthio-1,2-indanedione, which has the chemical structure depicted in Figure 3
6-nitro-1,2-indanedione, which has the chemical structure depicted in Figure 4
5-methoxy-1,2-indanedione, which has the chemical structure depicted in Figure 5
6-bromo-1,2-indanedione, which has the chemical structure depicted in Figure 6
5-chloro-1,2-indanedione, which has the chemical structure depicted in Figure 7
5,6-dimethoxy-1,2-indanedione, which has the chemical structure depicted in Figure 8
5-fluoro-1,2-indanedione, which has the chemical structure depicted in Figure 9
5,6-methylenedioxy-1,2-indanedione, which has the chemical structure depicted in Figure 10
5,6,7-trimethoxy-1,2-indanedione, which has the chemical structure depicted in Figure 11

The materials and methods used in the experiments presented in this Example are now described.

All reagents were purchased from Aldrich Chemical Co. (St. Louis, Mo.), except that n-butyl nitrite was synthesized as described (Blatt, 1946, Organic Synthesis, John Wiley & Sons, Inc., p. 654). Reagent grade methanol and zinc chloride were purchased from Fisher Scientific (Malvern, Pa.). DFO was purchased from Lightning Powder (Salem, Oreg.). Qualitative assessment and photography of fingerprints developed using DFO or a 1,2-indanedione derivative were illuminated using a 20 Watt argon ion laser fitted with an orange filter which transmits light having a wavelength greater than or equal to 530 nanometers.

Figure 21:
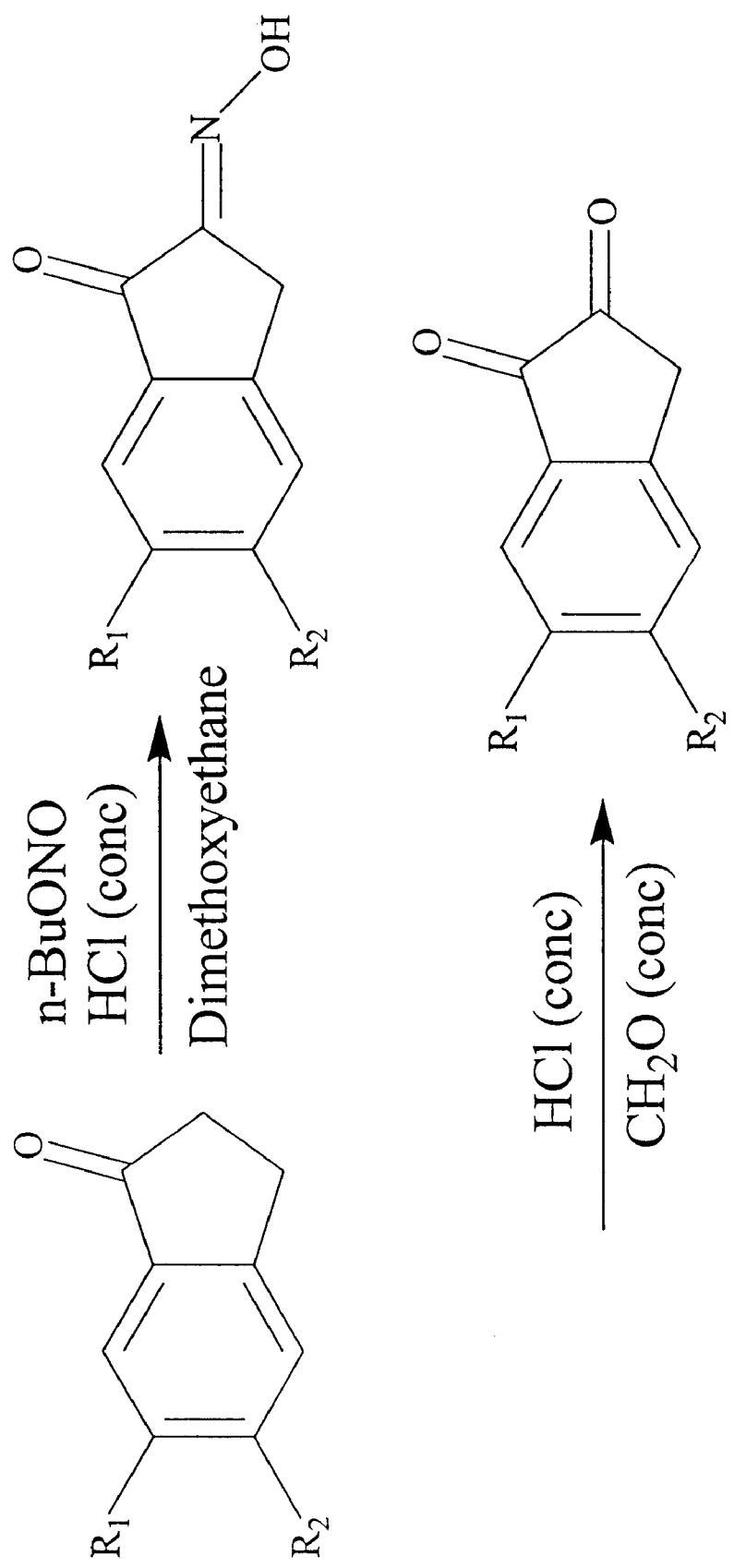
FIG. 21 illustrates a method of synthesizing a 1,2-indanedione derivative, the method involving acid hydrolysis of a 1,2-indanedione-2-oxime intermediate.

Synthesis of 1,2-Indanediones 1,2-Indanediones were synthesized essentially as illustrated in FIG. 21, by acid hydrolysis of corresponding 1,2-indanedione-2-oximes formed by α-oximation of corresponding 1-indanones. Some 1-indanones were commercially available, and others were synthesized from commercially available aldehydes substantially as illustrated in FIG. 20, according to known methods.

10 millimoles of a 1-indanone were dissolved in 8–16 milliliters of dimethoxyethane, depending on the solubility of the indanone. A volume of concentrated aqueous HCl equal to one third the volume of dimethoxyethane was added to the solution. After the solution was cooled to room temperature, 1.2 equivalents of freshly prepared n-butyl nitrite was added to the solution in a dropwise fashion while the solution was stirred. The temperature of the reaction mixture was maintained below 30° C. Formation of a creamy white or light yellow indan-1,2-dione-2-oxime precipitate was typically observed from about 10 to about 30 minutes after n-butyl nitrite addition was complete. Following addition of n-butyl nitrite, the reaction mixture was stirred for an additional 4–8 hours, and the precipitate, comprising 1,2-indanedione-2-oxime, was collected by suction filtration. The precipitate was washed three times with 20 milliliters of water and air dried. The yield of 1,2-indanedione-2-oxime from 1-indanone was typically between about 80 and about 90 percent. It was possible to improve the yield by diluting the mother liquor with water to precipitate additional oxime.

About 6 millimoles of the 1,2-indanedione-2-oxime was suspended in a mixture comprising 2 milliliters of 36% (v/v) aqueous formaldehyde and 4 milliliters of 37% (v/v) aqueous HCl, and the resulting suspension was stirred vigorously. Within about five or ten minutes, the suspension thickened, and the color of the suspension changed from light to dark yellow. The suspension was stirred for 4–8 hours, and the precipitate comprising a 1,2-indanedione derivative, was collected by suction filtration. The derivative was washed three times with 20 milliliters of water and air dried. The yield from this step was typically between about 80 and 95 percent. It was possible to improve the yield by diluting the mother liquor with water to precipitate additional derivative.

1,2-indanedione derivatives were used in the experiments presented in this Example in the form of 0.1% (w/v) solutions which were made by dissolving 50 milligrams of the 1,2-indanedione derivative in a mixture of 50 milliliters of methanol and 0.5 milliliter of glacial acetic acid. After dissolving the derivative in the mixture, 0.25 gram of zinc chloride was added to the solution. 5,6-Dimethoxy-1,2-indanedione was dissolved in 2 milliliters of methylene chloride prior to mixing this solution with the mixture of methanol and acetic acid and adding zinc chloride. DFO was prepared as a 1 millimolar solution in methanol which was acidified by adding 2% of the volume of the solution of glacial acetic acid.

Staining of Glycine Spots

Whatman filter paper was soaked in a 0.25% (w/v) solution of glycine in water and permitted to air dry for several days. Each of the methanolic solutions of a 1,2-indanedione derivative was applied separately to a piece of the glycine-soaked paper, using a capillary tube or brush to apply the solution. The DFO solution was similarly applied. A hand-held clothes iron was used to apply heat to each 1,2-indanedione- or DFO-treated paper by holding the iron from about 1 to about 2 centimeters from the paper for from about 20 to about 30 seconds. The iron was also used to apply steam to the 1,2-indanedione-treated papers, but not to the DFO-treated paper. Initial color development of 1,2-indanedione- and DFO-treated papers was assessed visually.

Absorbance and Fluorescence Assessment

Solutions used in absorbance and fluorescence determinations were as follows. Solutions of 1,2-indanedione derivatives comprised 1 millimolar derivative and 1% (v/v) glacial acetic acid in methanol. A solution of DFO comprised 1 millimolar DFO and 2% (v/v) glacial acetic acid in methanol. Glycine and zinc nitrate solutions comprised 0.5 millimolar glycine and 110 millimolar zinc nitrate in methanol, respectively.

The glycine solution was spotted onto Whatman filter paper, and the filter paper was permitted to dry. Next, the DFO solution or a 1,2-indanedione derivative solution was spotted onto the filter paper, and the filter paper was permitted to dry. The initial color was assessed visually. After this assessment, the zinc nitrate solution was spotted onto the filter paper. 1,2-Indanedione derivative-treated papers were developed by applying heat and steam using a hand-held clothes iron positioned from about one to about two centimeters from the paper for from about 20 to about 30 seconds. DFO-treated papers were developed in the same way, except that steam was not applied. Fluorescence measurements were made using a Hitachi model F-4500 fluorescence spectrophotometer.

Duration of Fluorescent Intensity

The method used to evaluate the duration of fluorescent intensity of an amine compound developed using DFO or a 1,2-indanedione derivative was a variation of the Nielson spot test method (Nielson, 1987, J. Forensic Sci. 32:370–376). The method involved spotting of a combination of two or more of a glycine solution, a DFO solution, a 1,2-indanedione derivative solution, and a zinc nitrate solution onto a Whatman filter paper substrate and subsequently examining color and fluorescence development under controlled conditions. The fluorescent intensity was assessed for a number of days to determine its duration.

To obtain the data presented in Table 3 herein, 10 microliters of a 0.5 millimolar glycine solution in methanol was spotted onto the substrate and dried. 10 microliters of either a 1 millimolar DFO solution in 2% (v/v) glacial acetic acid-acidified methanol or a 1 millimolar solution of a 1,2-indanedione solution in 1% (v/v) glacial acetic acid-acidified methanol was spotted onto the substrate and dried. Heat and steam were applied to the spots using a hand-held clothes iron for approximately a few seconds to accelerate development. Steam was not applied to the DFO-treated spots. Fluorescent intensity was measured on each of six consecutive days, "Day 1" being the day the reagents were applied to the substrate. "% Change" indicates the percentage difference between the fluorescent intensities on Day 1 and Day 6.

The data presented in Table 4 herein were obtained in the same manner as the data presented in Table 3, with the following differences. 10 Microliters of a 10 millimolar solution of zinc nitrate in methanol was applied to each spot. The duration of heat and steam application was approximately fifteen seconds.

The data presented in Table 5 herein were obtained in the same manner as the data presented in Table 3, with the following differences. All spots (i.e. including DFO-treated spots) were subjected to an environment wherein the temperature was 40° C. and the relative humidity was 80% for about one hour to accelerate development. No spots were treated using a hand-held clothes iron. Fluorescent intensity was measured on each of seven consecutive days. "% Change" indicates the percentage difference between the fluorescent intensities on Day 1 and Day 7.

Assessment of Fluorescence

Three dimensional fluorescence spectra were obtained using a Hitachi model F-4500 fluorescence spectrophotometer. A three dimensional spectrum is a plot of fluorescence excitation wavelength versus fluorescent emission wavelength versus fluorescent intensity. Samples were excited using radiation having a wavelength in the range from about 450 to about 600 nanometers, and fluorescent emission was assessed in the range of wavelengths from about 525 to about 725 nanometers. Fluorescent intensity is expressed herein in relative arbitrary units. The sample interval was 5 nanometers; the contour interval was 5 fluorescent intensity units; both the excitation and emission slits were set at 2.5 nanometers; the photomultiplier tube voltage was set at 400 volts. The scan speed was 30,000 nanometers per minute.

The results of the experiments presented in this Example are now described.

Staining of Glycine Spots

None of DFO and the 1,2-indanedione derivatives examined in this Example produced the intense color obtained using ninhydrin when applied to filter paper treated with glycine. The color obtained in most cases was a pale purple to pale pink, depending on the identity and the concentration of the compound used.

Treatment of glycine-treated filter paper that had been contacted with a 1,2-indanedione derivative with zinc generally changed the color of the spots from pale pink to a dark pink or pale purple color, depending upon the concentration of the derivative and the zinc cation. Considerable enhancement of both the color and the fluorescence of 1,2-indanedione derivatives was observed when zinc was incorporated into the composition comprising the derivative. It was observed that incorporation of zinc into the 1,2-indanedione derivative composition reduced the shelf life of the composition, suggesting that zinc should be mixed with the composition shortly before, simultaneously with, or after contact of the composition with an amine compound to be detected. It was further observed that addition of zinc to the 1,2-indanedione derivative composition increased the duration of fluorescence of amine compounds developed using 1,2-indanedione derivatives. Amine compounds developed using 1,2-indanedione derivatives in the absence of zinc generally decomposed rapidly over a few days, losing both color and fluorescence intensity. Such decomposition occurred only over a period of weeks or months when the 1,2-indanedione composition comprised zinc.

It was observed that the development conditions which yielded favorable results included steaming the amine compound contacted with a 1,2-indanedione derivative with a hand-held clothes iron for from about 20 to about 30 seconds. It was also observed that incorporation of 1% (v/v) glacial acetic acid in the 1,2-indanedione derivative composition improved amine compound development when the amine compound was on or in a paper substrate. It was noted that exposure of 1,2-indanedione derivative-treated papers to steam led to slight decomposition of the fluorescent product, but this effect was not observed with solutions containing zinc.

The solubility of 1,2-indanedione derivatives was generally higher than the solubility of DFO, which permits delivery of a greater quantity of amine-compound-staining agent per unit volume than is possible using DFO. A solution comprising from about 0.1–0.2% (w/v) was suitable for use in detecting amine compounds. Use of compositions comprising an equivalent concentration of DFO are not practical. The capacity of 1,2-indanedione derivatives to be used at higher concentrations than DFO permits more intense development of amine compounds, and thus detection of smaller quantities of amine compounds than is possible using DFO.

Absorbance and Fluorescence Assessment

The initial color of glycine-treated filter paper treated with DFO or a 1,2-indanedione derivative and the fluorescent properties of glycine-treated filter paper treated with zinc nitrate and either DFO or a 1,2-indanedione derivative are indicated in Table 2.

TABLE 2

Summary of Initial Color and Fluorescence Data for DFO and 1,2-Indanedione Derivatives. Fluorescent intensity ("F.I.") is expressed in relative arbitrary units.

| Reagent | Excitation Wavelength, nanometers | Emission Wavelength, nanometers | F.I. | Initial Color |
|---|---|---|---|---|
| DFO | 565 | 580 | 59 | Pink |
| 1,2-indanedione | 545 | 560 | 28 | lt. Pink |
| 6-methylthio-1,2-indanedione | 555 | 570 | 34 | lt. Orange |
| 6-nitro-1,2-indanedione | 545 | 560 | 11 | Tan |
| 5-methoxy-1,2-indanedione | 550 | 565 | 73 | lt. Pink |
| 6-bromo-1,2-indanedione | 550 | 560 | 77 | lt. Pink |
| 5-chloro-1,2-indanedione | 550 | 565 | 65 | lt. Pink |
| 5,6-dimethoxy-1,2-indanedione | 560 | 575 | 139 | Pink |
| 5-fluoro-1,2-indanedione | 545 | 560 | 11 | Purple |

Duration of Fluorescent Intensity

Fluorescent intensity values presented in Table 3 were obtained by treating glycine spots with either DFO or a 1,2-indanedione derivative and heating the treated spots briefly with a steam iron. The data presented in Table 4 represent glycine spots that were treated similarly, except that the spots were also treated with zinc. DFO-treated spots were not treated with steam. In nearly every case, the fluorescence intensity decreased over time. The decreases were more dramatic for spots not treated with zinc. Zinc treatment of spots treated with one of several 1,2-indanedione derivatives dramatically improved the fluorescence of the spots. Furthermore, zinc treatment of spots generally increased the duration of fluorescent intensity.

TABLE 3

Fluorescent Intensity Values of Glycine Spots Treated with DFO or a 1,2-Indanedione Derivative. Fluorescent intensity ("F.I.") is expressed in relative arbitrary units.

| | F.I. (Arb. Units) | | | | | | |
|---|---|---|---|---|---|---|---|
| | Day 1 | Day 2 | Day 3 | Day 4 | Day 5 | Day 6 | % Change |
| DFO | 50 | 44 | 40 | 37 | 34 | 35 | −30 |
| 1,2-indanedione | 20 | 19 | 16 | 15 | 13 | 12 | −38 |
| 5-methythio-1,2-indanedione | 28 | 25 | 20 | 19 | 17 | 19 | −31 |
| 6-nitro-1,2-indanedione | 11 | 10 | 9 | 10 | 11 | 10 | −12 |

TABLE 3-continued

Fluorescent Intensity Values of Glycine Spots Treated with DFO or a 1,2-Indanedione Derivative. Fluorescent intensity ("F.I.") is expressed in relative arbitrary units.

| | F.I. (Arb. Units) | | | | | | |
|---|---|---|---|---|---|---|---|
| | Day 1 | Day 2 | Day 3 | Day 4 | Day 5 | Day 6 | % Change |
| 5-methoxy-1,2-indanedione | 26 | 20 | 18 | 17 | 16 | 15 | −40 |
| 6-bromo-1,2-indanedione | 24 | 23 | 20 | 19 | 18 | 14 | −44 |
| 5-chloro-1,2-indanedione | 21 | 18 | 16 | 16 | 13 | 12 | −43 |
| 5-fluoro-1,2-indanedione | 10 | 10 | 10 | 10 | 9 | 9 | −9 |
| 5,6-dimethoxy-1,2-indanedione | 49 | 46 | 37 | 35 | 28 | 36 | −26 |

TABLE 4

Fluorescent Intensity Values of Glycine Spots Treated with Zinc and DFO or a 1,2-Indanedione Derivative. Fluorescent intensity ("F.I.") is expressed in relative arbitrary units.

| | F.I. (Arb. Units) | | | | | | |
|---|---|---|---|---|---|---|---|
| | Day 1 | Day 2 | Day 3 | Day 4 | Day 5 | Day 6 | % Change |
| DFO | 59 | 59 | 52 | 47 | 45 | 45 | −24 |
| 1,2-indanedione | 28 | 28 | 28 | 28 | 32 | 25 | −9 |
| 5-methythio-1,2-indanedione | 34 | 32 | 28 | 31 | 32 | 29 | −16 |
| 6-nitro-1,2-indanedione | 11 | 10 | 10 | 11 | 11 | 10 | −12 |
| 5-methoxy-1,2-indanedione | 73 | 75 | 69 | 68 | 68 | 60 | −18 |
| 6-bromo-1,2-indanedione | 77 | 78 | 68 | 72 | 68 | 55 | −28 |
| 5-chloro-1,2-indanedione | 65 | 69 | 62 | 63 | 53 | 44 | −32 |
| 5-fluoro-1,2-indanedione | 11 | 11 | 10 | 10 | 10 | 10 | −5 |
| 5,6-dimethoxy-1,2-indanedione | 138 | 143 | 136 | 153 | 152 | 142 | +3 |

Fluorescent intensity values obtained by treating glycine spots with either DFO or a 1,2-indanedione derivative and subjecting the spots to heat and humidity are presented in Table 5. The data presented in Table 6 represent glycine spots that were treated similarly, except that the spots were also treated with zinc. Subjecting the spots to heat and humidity decreased the fluorescent intensity of DFO-treated spots, but dramatically increased the fluorescent intensity of spots treated with 5,6-dimethoxy-1,2-indanedione. Treatment of the spots with zinc further increased the fluorescent intensity of the spots. The rate of decrease of the fluorescent intensity of heat- and humidity-treated spots was generally higher than the rate corresponding to spots treated with a hand-held iron.

TABLE 5

Fluorescent Intensity Values of Glycine Spots Treated with DFO or a 1,2-Indanedione Derivative and Subjected to Heat and Humidity. Fluorescent intensity ("F.I.") is expressed in relative arbitrary units.

| | F.I. (Arb. Units) | | | | | | | % |
|---|---|---|---|---|---|---|---|---|
| | Day 1 | Day 2 | Day 3 | Day 4 | Day 5 | Day 6 | Day 7 | Change |
| DFO | 32 | 30 | 30 | 27 | 23 | 24 | 19 | −39 |
| 1,2-indanedione | 15 | 15 | 15 | 15 | 14 | 14 | 13 | −14 |
| 5-methythio-1,2-indanedione | 28 | 24 | 21 | 21 | 17 | 17 | 16 | −44 |
| 6-nitro-1,2-indanedione | 12 | 12 | 12 | 13 | 12 | 12 | 12 | −1 |
| 5-methoxy-1,2-indanedione | 25 | 25 | 22 | 21 | 18 | 18 | 14 | −44 |
| 6-bromo-1,2-indanedione | 21 | 21 | 20 | 20 | 17 | 17 | 15 | −32 |
| 5-chloro-1,2-indanedione | 15 | 15 | 15 | 16 | 14 | 14 | 13 | −16 |
| 5-fluoro-1,2-indanedione | 12 | 13 | 13 | 14 | 12 | 12 | 12 | −23 |
| 5,6-dimethoxy-1,2-indanedione | 116 | 92 | 86 | 69 | 56 | 50 | 34 | −71 |

TABLE 6

Fluorescent Intensity Values of Glycine Spots Treated with Zinc and DFO or a 1,2-Indanedione Derivative and Subjected to Heat and Humidity. Fluorescent intensity ("F.I.") is expressed in relative arbitrary units.

| | F.I. (Arb. Units) | | | | | | | % |
|---|---|---|---|---|---|---|---|---|
| | Day 1 | Day 2 | Day 3 | Day 4 | Day 5 | Day 6 | Day 7 | Change |
| DFO | 60 | 56 | 45 | 40 | 38 | 38 | 31 | −48 |
| 1,2-indanedione | 45 | 42 | 35 | 35 | 31 | 29 | 23 | −49 |
| 5-methythio-1,2-indanedione | 59 | 52 | 45 | 39 | 33 | 34 | 23 | −61 |
| 6-nitro-1,2-indanedione | 13 | 13 | 13 | 14 | 12 | 13 | 12 | −3 |
| 5-methoxy-1,2-indanedione | 146 | 154 | 129 | 116 | 96 | 96 | 70 | −50 |
| 6-bromo-1,2-indanedione | 95 | 93 | 81 | 83 | 72 | 68 | 51 | −46 |
| 5-chloro-1,2-indanedione | 68 | 62 | 51 | 54 | 45 | 45 | 28 | −58 |
| 5-fluoro-1,2-indanedione | 13 | 13 | 13 | 14 | 13 | 13 | 13 | +1 |
| 5,6-dimethoxy-1,2-indanedione | 346 | 354 | 302 | 317 | 276 | 274 | 240 | −30 |

Figure 23:
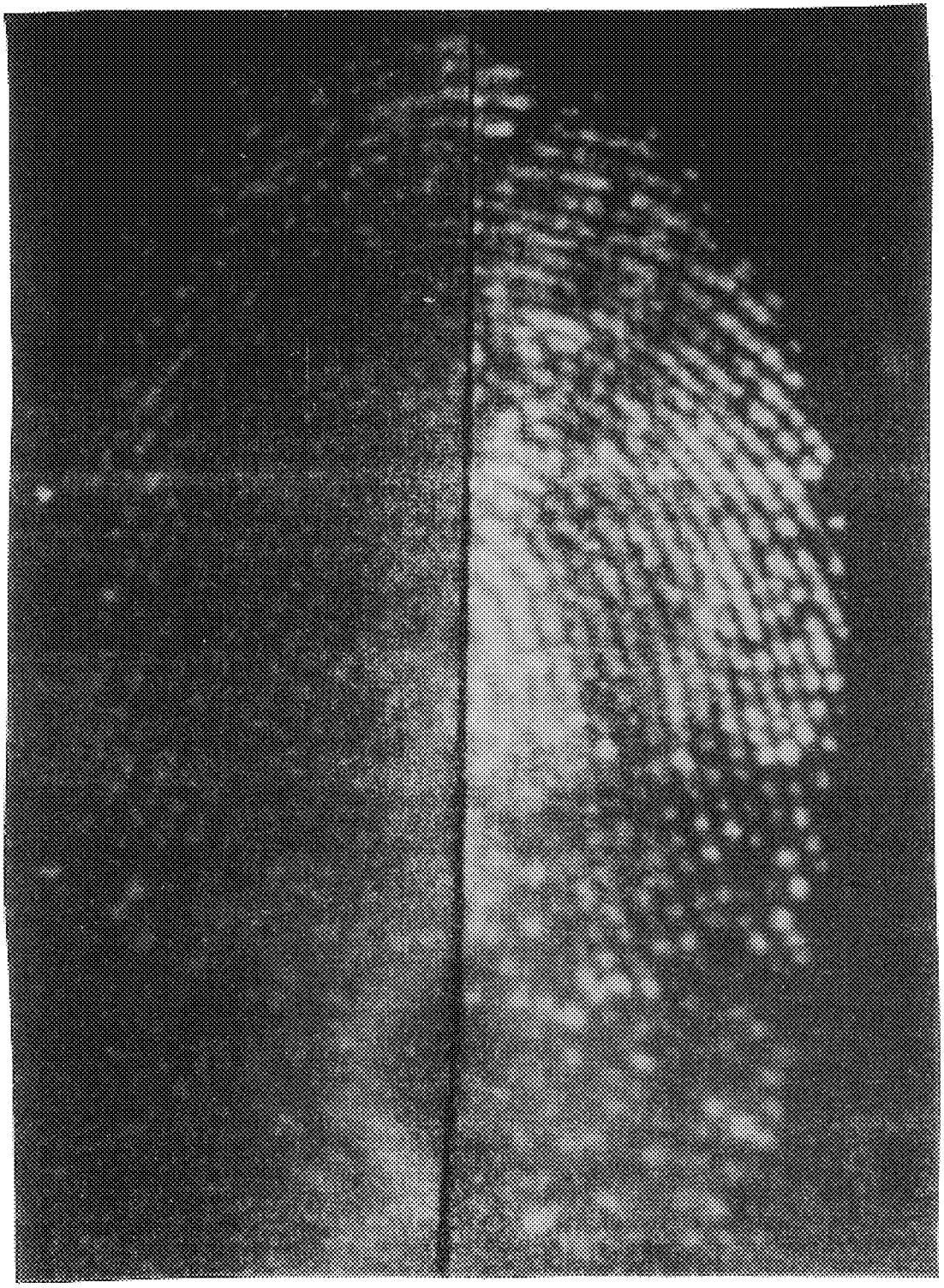
FIG. 23, comprising Panels A and B, is a pair of images of halves of the same fingerprint which were developed using a prior art compound and using a 1,2-indanedione derivative. In Panel A, the left half of the fingerprint was developed using a composition comprising 1 millimolar DFO in methanol which was acidified with 2% (v/v) glacial acetic acid, applying heat and humidity to the print, and illuminating the print; fluorescently emitted light was recorded using a camera. In Panel B, the right half of the fingerprint was developed using a composition comprising 1 millimolar 5,6-dimethoxy-1,2-indanedione in methanol which was acidified with 2% (v/v) glacial acetic acid, applying heat and humidity to the print, and illuminating the print; fluorescently emitted light was recorded using a camera.
Figure 24:
FIG. 24 is an image of a fingerprint developed using a composition comprising 100 millimolar 5,6-dimethoxy-1,2-indanedione in methanol which was acidified with 2% (v/v) glacial acetic acid, applying heat and humidity to the print, and illuminating the print; fluorescently emitted light was recorded using a camera.
Figure 25:
FIG. 25, comprising Panels A and B, is a pair of images of halves of the same fingerprint which were developed using, in Panel A, DFO, and, in Panel B, 5,6-dimethoxy-1,2-indanedione. Compositions and conditions are described in the Example herein.
Figure 26:
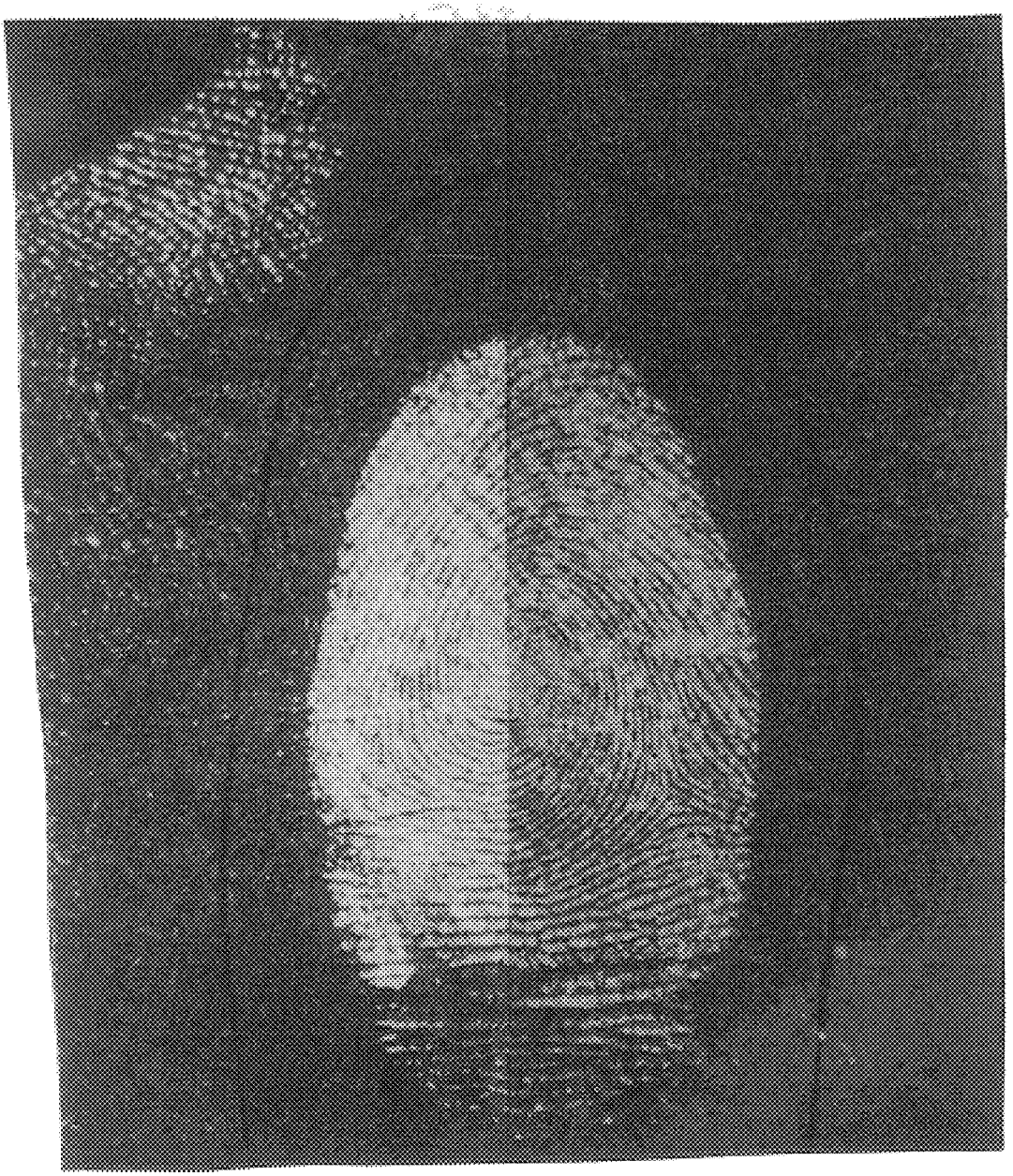
FIG. 26, comprising Panels A and B, is a pair of images of halves of the same fingerprint which were developed using, in Panel A, 5,6-dimethoxy-1,2-indanedione and zinc nitrate, and, in Panel B, 5,6-dimethoxy-1,2-indanedione alone.

As illustrated in FIGS. 23 and 25, the fluorescent intensities of the halves a fingerprint were approximately equal when the fingerprint was developed using 1 millimolar DFO on half of the fingerprint and 1 millimolar 5,6-dimethoxy-1,2-indanedione on the other half. As illustrated in FIG. 24, a similarly-obtained fingerprint developed using 100 millimolar 5,6-dimethoxy-1,2-indanedione and zinc exhibited significantly greater fluorescent intensity. Furthermore, as illustrated in FIG. 26, the fluorescent intensity of the half a fingerprint developed using 5,6-dimethoxy-1,2-indanedione and zinc was significantly greater than the fluorescent intensity of the other half the fingerprint, which was developed using 5,6-dimethoxy-1,2-indanedione alone.

The best results were obtained using fingerprints or spots developed using 5,6-dimethoxy-1,2-indanedione or 5,6-methylenedioxy-1,2-indanedione and treated with zinc. Before treatment with a zinc cation, the fluorescence of such prints or spots was marginally better than the fluorescence obtained using DFO. However, after treating the prints or spots with zinc, the fluorescent intensity of the spots significantly exceeded that of DFO-treated prints or spots.

DFO is presently one of the most widely-used latent fingerprint detection reagents among law enforcement and forensic science agencies. Many of these agencies possess the equipment needed to observe DFO-developed fingerprints, including an optical filter which transmits substantially no light having a wavelength greater than about 530 nanometers (i.e. a green filter), an optical filter which transmits substantially no light having a wavelength less than about 550 nanometers (i.e. a red filter), a light source, and a recorder such as a camera. Thus, these agencies are equipped to observe 1,2-indanedione derivative-developed fingerprints. Because 1,2-indanedione derivatives can be produced at a cost lower than that of DFO, and because the sensitivity of 1,2-indanedione fingerprint derivative detection is greater than the sensitivity of DFO fingerprint detection, 1,2-indanedione compositions and methods of detecting latent fingerprints using such compositions are superior to DFO for detecting latent fingerprints.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of detecting the presence of an amine compound in a fingerprint, the method comprising contacting the amine compound with a composition comprising a molecule having the chemical structure of Formula I to form a product,

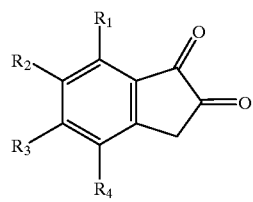

(I)

wherein each of $R_1$, $R_2$, $R_3$, and $R_4$ is independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, an aryloxy substituent, an alkenyloxy substituent, a dialkylamino substituent, an arylalkylamino substituent, a diarylamino substituent, an alkenylamino substituent, a sulffiydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent, and wherein any adjacent two of $R_1$, $R_2$, $R_3$, and $R_4$ can, together, be a cyclic substituent;

assessing an optical property of the product, wherein the optical property is selected from the group consisting of absorbance and fluorescence, and comparing the optical property of the product with the same optical property of the composition, whereby a difference between the optical property of the product and the same optical property of the composition is an indication that the amine compound is present.

2. The method of claim 1, wherein $R_2$ is neither of a nitro substituent and a nitroso substituent; and wherein the molecule is not 1,2-indanedione.

3. The method of claim 1, wherein the composition further comprises a group IIB metal cation.

4. The method of claim 3, wherein the group IIB metal cation is a zinc cation.

5. The method of claim 1, further comprising contacting the product with a group IIB metal cation prior to detecting fluorescence.

6. The method of claim 1, wherein contacting the amine compound with the composition comprises applying the composition to a surface having the fingerprint thereon, and wherein assessing an optical property of the product comprises illuminating the surface and observing the presence or absence of fluorescence.

7. The method of claim 1, wherein assessing an optical property of the product comprises illuminating the product using an electromagnetic radiation source which emits electromagnetic radiation having a wavelength less than about 530 nanometers.

8. The method of claim 7, further comprising detecting electromagnetic radiation emitted from the product having a wavelength greater than about 550 nanometers.

9. The method of claim 1, further comprising applying heat and humidity to the product prior to assessing the optical property.

10. The method of claim 9, wherein applying heat and humidity to the product comprises maintaining the product at about 40° C. and about 80% relative humidity for about one hour.

11. The method of claim 1, wherein the molecule is 1,2-indanedione.

12. The method of claim 1, wherein the molecule is 6-methylthio-1,2-indanedione.

13. The method of claim 1, wherein the molecule is 6-trimethylsilyl-1,2-indanedione.

14. The method of claim 1, wherein the molecule is 6-nitro-1,2-indanedione.

15. The method of claim 1, wherein the molecule is 5-methoxy-1,2-indanedione.

16. The method of claim 1, wherein the molecule is 6-bromo-1,2-indanedione.

17. The method of claim 1, wherein the molecule is 5-chloro-1,2-indanedione.

18. The method of claim 1, wherein the molecule is 5,6,-dimethoxy-1,2-indanedione.

19. The method of claim 1, wherein the molecule is 5-fluoro-1,2-indanedione.

20. The method of claim 1, wherein the molecule is 6-(2-thienyl)-1,2-indanedione.

21. The method of claim 1, wherein the molecule is 6-(3-thienyl)-1,2-indanedione.

22. The method of claim 1, wherein the molecule is thieno[f]-1,2-indanedione.

23. The method of claim 1, wherein the molecule is thieno[f]-2,3-indanedione.

24. The method of claim 1, wherein the molecule is 5,6-methylenedioxy-1,2-indanedione.

25. The method of claim 1, wherein the molecule is 5,6,7-trimethoxy-1,2-indanedione.

26. The method of claim 1, wherein the molecule is a 2,2-substituted-1,3-dioxa-2-sila-cyclopenta[d]5,6-indanedione.

27. The method of claim 1, wherein the molecule is 2,2-dimethyl-1,3-dioxa-2-sila-cyclopenta[d]5,6-indanedione.

28. The method of claim 1, wherein the molecule is indeno[2,3-e]benzofuran-1,2-dione.

29. The method of claim 1, wherein $R_1$ is selected from the group consisting of a hydrogen atom and a methoxy substituent;

$R_2$ is selected from the group consisting of a hydrogen atom, a halogen atom, a nitro substituent, a methoxy substituent, an alkylthio substituent, and an arylthio substituent;

$R_3$ is selected from the group consisting of a hydrogen atom, a halogen atom, and a methoxy substituent; and R$_4$ is a hydrogen atom.

30. A method of detecting a fingerprint on a surface, the method comprising applying a composition to the surface, the composition comprising a molecule having the chemical structure of Formula I

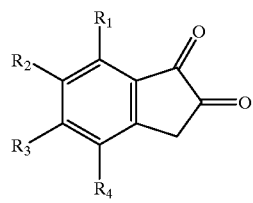

(I)

wherein each of R$_1$, R$_2$, R$_3$, and R$_4$ is independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent, and wherein two of R$_1$, R$_2$, R$_3$ and R$_4$ can be the same substituent, illuminating the surface, and assessing the presence or absence of fluorescence from the illuminated surface, whereby the fingerprint is detected by the presence of fluorescence emitted from the illuminated surface.

31. The method of claim 30, wherein

R$_1$ is selected from the group consisting of a hydrogen atom and a methoxy substituent;

R$_2$ is selected from the group consisting of a hydrogen atom, a halogen atom, a nitro substituent, a methoxy substituent, an alkylthio substituent, and an arylthio substituent;

R$_3$ is selected from the group consisting of a hydrogen atom, a halogen atom, and a methoxy substituent; and R$_4$ is a hydrogen atom.

32. A method of recording the pattern of a latent fingerprint on a surface, the method comprising applying a composition comprising a molecule having the chemical structure of Formula I

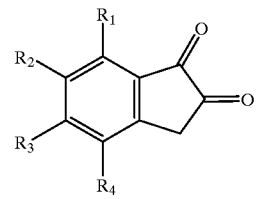

(I)

wherein each of R$_1$, R$_2$, R$_3$, and R$_4$ is independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent, and wherein two of R$_1$, R$_2$, R$_3$, and R$_4$ can be the same substituent, illuminating the surface, whereby a fluorescence pattern is emitted from the surface, and recording the fluorescence pattern, whereby the pattern of the fingerprint is recorded.

33. The method of claim 32, wherein

R$_1$ is selected from the group consisting of a hydrogen atom and a methoxy substituent;

R$_2$ is selected from the group consisting of a hydrogen atom, a halogen atom, a nitro substituent, a methoxy substituent, an alkylthio substituent, and an arylthio substituent;

R$_3$ is selected from the group consisting of a hydrogen atom, a halogen atom, and a methoxy substituent; and R$_4$ is a hydrogen atom.

34. A kit for detecting the presence of an amine compound in a fingerprint on a surface, the kit comprising an applicator and a composition of matter comprising a molecule having a chemical structure defined by formula I:

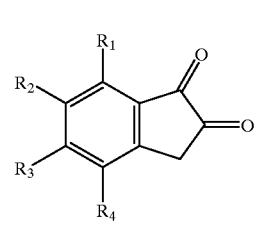

(I)

wherein R$_1$ and R$_4$ are independently selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an alkoxy substituent, an aryloxy substituent, an alkenyloxy substituent, a dialkylamino substituent, an arylalkylamino substituent, a diarylamino substituent, an alkenylarnino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent;

wherein $R_2$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent;

wherein $R_3$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylarnino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted axyl substituent, and an unsubstituted heteroaryl substituent, wherein the molecule is not 1,2-indanedione;
wherein any adjacent two of $R_1$, $R_2$, $R_3$, and $R_4$ can, together, be a cyclic substituent; and
wherein the applicator is selected from the group consisting of a capillary tube, a brush, an atomizer, a sponge, an absorbent material, a film, and a plate.

35. The kit of claim 34, wherein the composition further comprises a group IIB metal cation.

36. The kit of claim 34, further comprising a second composition comprising a group IIB metal cation.

37. The kit of claim 34, wherein
$R_1$ is selected from the group consisting of a hydrogen atom and a methoxy substituent;
$R_2$ is selected from the group consisting of a hydrogen atom, a halogen atom, an alkylthio substituent, and an arylthio substituent;
$R_3$ is selected from the group consisting of a hydrogen atom and a halogen atom; and
$R_4$ is a hydrogen atom.

38. A composition of matter comprising a molecule having a chemical structure defined by formula I:

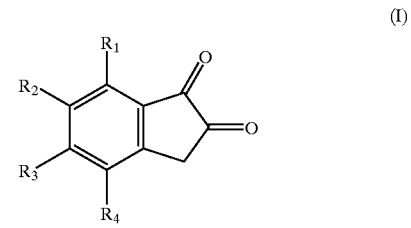

(I)

wherein each of $R_1$ and $R_4$ is a hydrogen atom;
wherein $R_2$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, and an unsubstituted heteroaryl substituent;

wherein $R_3$ is selected from the group consisting of a hydrogen atom, a halogen atom, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, and an unsubstituted heteroaryl substituent; and wherein the molecule is not 1,2-indanedione.

39. The composition of claim 38, wherein each of $R_2$ and $R_3$ is independently selected from the group consisting of a hydrogen atom and a halogen atom.

40. The composition of claim 38, wherein
each of $R_1$ and $R_4$ is a hydrogen atom;

R$_2$ is selected from the group consisting of a hydrogen atom, a halogen atom, an alkylthio substituent, and an arylthio substituent; and R$_3$ is selected from the group consisting of a hydrogen atom and a halogen atom.

41. A composition of matter comprising a molecule having a chemical structure defined by formula I:

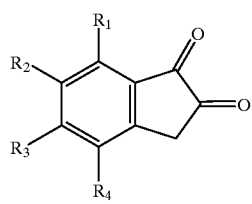

(I)

wherein R$_1$ and R$_4$ are independently selected from the group consisting of a hydrogen atom, a methoxy substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent;

wherein R$_2$ is selected from the group consisting of a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an aryloxy substituent, an alkenyloxy substituent, a dialkylamino substituent, at arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, and an unsubstituted heteroaryl substituent;

wherein R$_3$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, and an unsubstituted heteroaryl substituent; and wherein any adjacent two of R$_1$, R$_2$, R$_3$, and R$_4$ can together, be a cyclic substituent.

42. The composition of claim 41, further comprising a group IIB metal cation.

43. The composition of claim 41, wherein the molecule is 6-methylthio-1,2-indanedione.

44. The composition of claim 41, wherein the molecule is 6-trimethylsilyl-1,2-indanedione.

45. The composition of claim 41, wherein the molecule is 6-bromo-1,2-indanedione.

46. The composition of claim 41, wherein the molecule is 5-chloro-1,2-indanedione.

47. The composition of claim 41, wherein the molecule is 5-fluoro-1,2-indanedione.

48. The composition of claim 41, wherein the molecule is 6-(2-thienyl)-1,2-indanedione.

49. The composition of claim 41, wherein the molecule is 6-(3-thienyl)-1,2-indanedione.

50. The composition of claim 41, wherein the molecule is thieno[f]-1,2-indanedione.

51. The composition of claim 41, wherein the molecule is thieno[f]-2,3-indanedione.

52. The composition of claim 41, wherein the molecule is a 2,2-substituted-1,3-dioxa-2-sila-cyclopenta[d]5,6-indanedione.

53. The composition of claim 41, wherein the molecule is 2,2-dimethyl-1,3-dioxa-2-sila-cyclopenta[d]5,6-indanedione.

54. The composition of claim 41, wherein the molecule is indeno[2,3-e]benzofuran-1,2-dione.

55. The composition of claim 41, wherein

R$_1$ is selected from the group consisting of a hydrogen atom and a methoxy substituent;

R$_2$ is selected from the group consisting of a halogen atom, an alkylthio substituent, and an arylthio substituent;

R$_3$ is selected from the group consisting of a hydrogen atom and a halogen atom; and R$_4$ is a hydrogen atom.

56. A composition of matter comprising a molecule having a chemical structure defined by formula I:

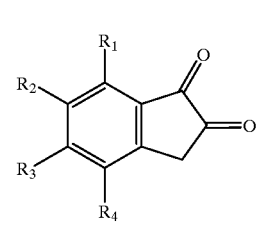

(I)

wherein R$_1$ and R$_4$ are independently selected from the group consisting of a hydrogen atom, a methoxy substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent;

wherein each of R$_2$ and R$_3$ is a methoxy substituent; and wherein at least one of R$_1$ and R$_4$ is not hydrogen.

57. The composition of claim 56, wherein the molecule is 4,5,6-trimethoxy-1,2-indanedione.

58. The composition of claim 56, wherein the molecule is 5,6,7-trimethoxy-1,2-indanedione.

59. A kit for detecting the presence of an amine compound in a fingerprint on a surface, the kit comprising an applicator and a composition of matter comprising a molecule having a chemical structure defined by formula I:

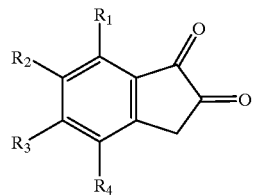

(I)

wherein $R_1$ and $R_4$ are independently selected from the group consisting of a hydrogen atom, a methoxy substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent;

wherein $R_2$ is selected from the group consisting of a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamnino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, and an unsubstituted heteroaryl substituent;

wherein $R_3$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a nitto substituent, a nitroso substituent, a boronic acid substituent, a boric acid ester substituent, a dihydroxyphosphonyl substituent, a hydroxy substituent, an alkoxy substituent, an aryloxy substituent, an alkenyloxy substituent, a dialkylamino substituent, an arylalkylamino substituent, a diarylamino substituent, an alkenylarnino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an alkylsilyloxy substituent, an unsubstituted aryl substituent, and an unsubstituted heteroaryl substituent; and wherein any adjacent two of $R_1$, $R_2$, $R_3$, and $R_4$ can together, be a cyclic substituent.

60. The kit of claim 59, wherein $R_1$ is selected from the group consisting of a hydrogen atom and a methoxy substituent;

$R_2$ is selected from the group consisting of a halogen atom, an alkylthio substituent, and an arylthio substituent;

$R_3$ is selected from the group consisting of a hydrogen atom, and a halogen atom, and a methoxy substituent; and $R_4$ is a hydrogen atom.

61. A composition of matter comprising a molecule having a chemical structure defined by formula I:

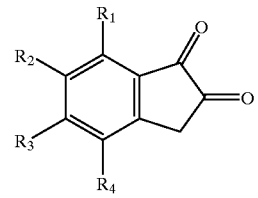

(I)

wherein $R_1$ is selected from the group consisting of a hydrogen atom, a halogen atom, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent;

wherein $R_2$ is selected from the group consisting of a hydrogen atom, a halogen atom, an alkyl substituent, an alkenyl substituent, a carboxy substituent, a carboalkoxy substituent, a carbaldehyde substituent, an oxo substituent, a cyano substituent, a thiocyano substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, and an unsubstituted heteroaryl substituent;

wherein $R_3$ is selected from the group consisting of a hydrogen atom, a halogen atom, an alkenyl substituent, a carboxy substituent, a carboalkoxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, and an unsubstituted heteroaryl substituent;

wherein $R_4$ is selected from the group consisting of a hydrogen atom, a halogen atom, an alkenyl substituent, a carboxy substituent, a carbaldehyde substituent, an oxo substituent, a cyano substituent, a thiocyano substituent, a nitro substituent, a nitroso substituent, a boronic acid substituent, a boric acid ester substituent, a dihydroxyphosphonyl substituent, a hydroxy substituent, an aryloxy substituent, an alkenyloxy substituent, a dialkylamino substituent, an arylalkylamino substituent, a diarylamino substituent, an alkenylamino substituent, a sulfhydryl substituent, an alkylthio substituent, an arylthio substituent, an alkenylthio substituent, a sulfonate substituent, a silyl substituent, an alkylsilyl substituent, an alkylarylsilyl substituent, an arylsilyl substituent, a siloxy substituent, an alkylsilyloxy substituent, an arylsilyloxy substituent, an unsubstituted aryl substituent, a substituted aryl substituent, and an unsubstituted heteroaryl substituent; and wherein the molecule is not 1,2-indanedione.

62. The composition of claim 61, wherein each of $R_1$ and $R_4$ is a hydrogen atom;

$R_2$ is selected from the group consisting of a hydrogen atom, a halogen atom, an alkylthio substituent, and an arylthio substituent; and $R_3$ is selected from the group consisting of a hydrogen atom and a halogen atom.

* * * * *